(12) United States Patent
Gladish et al.

(10) Patent No.: US 12,193,521 B2
(45) Date of Patent: Jan. 14, 2025

(54) SLEEVE FOR AN EXTREMITY

(71) Applicant: NIKE, Inc., Beaverton, OR (US)

(72) Inventors: Justin Lee Gladish, Portland, OR (US); Naomi Morrison, Beaverton, OR (US); Trina Z. Murrietta, Portland, OR (US); Carissa J. Rozinka, Portland, OR (US); Todd A. Waatti, Battle Ground, WA (US); Lawrence Yow Yun, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 278 days.

(21) Appl. No.: 17/525,597

(22) Filed: Nov. 12, 2021

(65) Prior Publication Data

US 2022/0205152 A1 Jun. 30, 2022

Related U.S. Application Data

(60) Provisional application No. 63/164,677, filed on Mar. 23, 2021, provisional application No. 63/157,890, (Continued)

(51) Int. Cl.

| A41B 11/02 | (2006.01) |
|---|---|
| A41B 11/00 | (2006.01) |
| A61F 2/78 | (2006.01) |
| D04B 1/10 | (2006.01) |
| D04B 1/18 | (2006.01) |
| D04B 1/26 | (2006.01) |

(52) U.S. Cl.
CPC ............ *A41B 11/02* (2013.01); *A41B 11/003* (2013.01); *A61F 2/7812* (2013.01); *D04B 1/102* (2013.01); *D04B 1/18* (2013.01); *D04B 1/265* (2013.01); *A61F 2002/7837* (2013.01); *D10B 2401/041* (2013.01); *D10B 2509/00* (2013.01)

(58) Field of Classification Search
None
See application file for complete search history.

(56) References Cited

U.S. PATENT DOCUMENTS

| 1,806,492 A | 5/1931 | Nestler |
|---|---|---|
| 2,050,535 A | 8/1936 | Martel |

(Continued)

FOREIGN PATENT DOCUMENTS

| CN | 104413996 A | 3/2015 |
|---|---|---|
| CN | 106048869 A | 10/2016 |

(Continued)

OTHER PUBLICATIONS

"Nanofront." Teijin Frontier Co, Ltd. Aug. 4, 2008. https://www2.teijin-frontier.com/english/product/old/specifics/nanofront.html (Year: 2008).*

(Continued)

*Primary Examiner* — Grace Huang
(74) *Attorney, Agent, or Firm* — Shook, Hardy & Bacon L.L.P.

(57) ABSTRACT

Aspects herein are directed to a tubular knit sleeve for a below-the-knee amputee where the tubular knit sleeve includes zoned grip features, zoned cushioning features, zoned traction features, and zoned breathability/permeability features that facilitate the wearer participating in athletic activities, such as wrestling, without a prosthetic leg.

19 Claims, 11 Drawing Sheets

Related U.S. Application Data filed on Mar. 8, 2021, provisional application No. 63/132,593, filed on Dec. 31, 2020.

(56) References Cited

U.S. PATENT DOCUMENTS

| | | | |
|---|---|---|---|
| 2,102,368 A | 12/1937 | Martel | |
| 2,279,919 A | 4/1942 | Harry | |
| 2,728,210 A * | 12/1955 | Stevens | D04B 1/126 |
| | | | 66/227 |
| 2,926,512 A | 3/1960 | Robertson | |
| 3,130,566 A | 4/1964 | Chesebro | |
| 3,601,818 A | 8/1971 | Chesebro et al. | |
| 3,793,851 A | 2/1974 | Thorneburg | |
| 3,975,929 A | 8/1976 | Fregeolle | |
| 3,991,424 A | 11/1976 | Prahl | |
| 4,034,580 A | 7/1977 | Holder | |
| 4,034,581 A | 7/1977 | Swafford | |
| 4,038,699 A | 8/1977 | Burn | |
| 4,104,892 A | 8/1978 | Thorneburg | |
| 4,149,274 A | 4/1979 | Garrou et al. | |
| 4,237,707 A | 12/1980 | Coble et al. | |
| 4,282,727 A | 8/1981 | Dunlap et al. | |
| 4,282,728 A | 8/1981 | Tapp et al. | |
| 4,326,393 A | 4/1982 | Dunlap | |
| 4,341,096 A | 7/1982 | Safrit et al. | |
| 4,470,250 A * | 9/1984 | Arenz | D02G 3/328 |
| | | | 57/225 |
| 4,494,388 A | 1/1985 | Lau et al. | |
| 4,514,863 A | 5/1985 | Tuyet-van | |
| 4,520,635 A | 6/1985 | Shields et al. | |
| 4,522,044 A | 6/1985 | Lineberry et al. | |
| 4,561,267 A * | 12/1985 | Wilkinson | D04B 1/26 |
| | | | 66/178 A |
| 4,702,091 A | 10/1987 | Good et al. | |
| 4,732,015 A | 3/1988 | Abrams et al. | |
| 4,986,090 A | 1/1991 | Lombardi | |
| 4,998,419 A | 3/1991 | Moore | |
| 5,307,522 A | 5/1994 | Throneburg et al. | |
| 5,335,517 A * | 8/1994 | Throneburg | A43B 17/18 |
| | | | 66/49 |
| 5,412,957 A * | 5/1995 | Bradberry | A61F 13/08 |
| | | | 66/178 A |
| 5,428,975 A | 7/1995 | Lee et al. | |
| 5,603,232 A | 2/1997 | Throneburg | |
| 5,708,985 A | 1/1998 | Ogden | |
| 5,809,575 A | 9/1998 | Chen | |
| 5,931,872 A | 8/1999 | Lohmann | |
| 6,079,235 A | 6/2000 | Schmidt | |
| 6,149,690 A * | 11/2000 | Belzidsky | A61F 2/7812 |
| | | | 623/32 |
| 6,324,874 B2 | 12/2001 | Fujimoto | |
| 6,592,539 B1 * | 7/2003 | Einarsson | A61F 5/0109 |
| | | | 623/32 |
| 6,684,412 B2 * | 2/2004 | Ricci | A61F 13/08 |
| | | | 66/178 A |
| 6,708,342 B2 | 3/2004 | Boersema | |
| 6,871,516 B2 | 3/2005 | Peeler et al. | |
| D503,802 S | 4/2005 | Bjarnason | |
| 6,964,688 B1 | 11/2005 | Kania | |
| 7,076,973 B1 | 7/2006 | Chesebro et al. | |
| 7,169,189 B2 | 1/2007 | Bjarnason et al. | |
| D590,590 S | 4/2009 | Bonzagni et al. | |
| 7,677,061 B2 | 3/2010 | Mori et al. | |
| 7,699,195 B2 | 4/2010 | Scott | |
| 7,748,240 B1 | 7/2010 | Cherneski | |
| 7,765,835 B2 * | 8/2010 | Karayianni | D02G 3/328 |
| | | | 66/172 E |
| D634,925 S | 3/2011 | Gesser et al. | |
| D643,207 S | 8/2011 | Hollingsworth et al. | |
| 8,051,498 B2 | 11/2011 | Ganzoni et al. | |
| 8,220,077 B1 | 7/2012 | Ott et al. | |
| 8,490,218 B1 * | 7/2013 | Thompson | A41B 11/004 |
| | | | 66/185 |
| 8,491,515 B2 * | 7/2013 | Schneider | A61F 2/7812 |
| | | | 602/62 |
| 8,544,300 B2 | 10/2013 | Kaneda et al. | |
| D740,014 S | 10/2015 | Amis | |
| 9,192,200 B2 * | 11/2015 | Matsuo | D04B 1/102 |
| D747,601 S | 1/2016 | Middleton | |
| 9,301,552 B2 | 4/2016 | Dickson | |
| 9,358,172 B2 | 6/2016 | Collins et al. | |
| D762,057 S | 7/2016 | Hakeem | |
| D773,798 S | 12/2016 | Amis | |
| 9,526,651 B2 * | 12/2016 | Kozasa | D04B 1/26 |
| D776,913 S | 1/2017 | Hakeem | |
| 9,565,877 B2 * | 2/2017 | Martinet | A41C 3/065 |
| 9,603,748 B2 | 3/2017 | Valois et al. | |
| 10,011,926 B2 | 7/2018 | Gaither | |
| 10,076,436 B2 * | 9/2018 | Jones | A43B 7/1445 |
| 10,271,968 B2 | 4/2019 | Bache et al. | |
| 10,376,391 B2 | 8/2019 | Halldorsson et al. | |
| 10,422,058 B2 * | 9/2019 | Rockstroh | D04B 1/24 |
| 10,456,287 B2 * | 10/2019 | Shaffer | A61F 5/0127 |
| 10,472,742 B1 * | 11/2019 | May | D02G 3/441 |
| 10,501,874 B2 | 12/2019 | Kostian | |
| D895,264 S | 9/2020 | Manning et al. | |
| 10,797,286 B2 * | 10/2020 | Morin | H01G 11/52 |
| 11,008,681 B2 * | 5/2021 | Lawrence | D04B 21/04 |
| 11,369,496 B2 * | 6/2022 | Asgeirsson | A61F 2/7812 |
| 11,401,636 B2 | 8/2022 | Amis et al. | |
| 11,560,651 B2 * | 1/2023 | Rock | D04B 1/102 |
| 11,849,773 B2 * | 12/2023 | Morgan | D03D 1/0043 |
| 2005/0149202 A1 | 7/2005 | Schaffer et al. | |
| 2007/0029308 A1 * | 2/2007 | Arabeyre | D02G 3/328 |
| | | | 219/545 |
| 2007/0033711 A1 * | 2/2007 | Achtelstetter | A41B 11/00 |
| | | | 2/239 |
| 2007/0162153 A1 | 7/2007 | Barnes et al. | |
| 2008/0034478 A1 | 2/2008 | Patterson | |
| 2008/0041113 A1 | 2/2008 | Mori et al. | |
| 2009/0031582 A1 | 2/2009 | Lu | |
| 2009/0076625 A1 | 3/2009 | Groves et al. | |
| 2009/0132056 A1 | 5/2009 | Kania | |
| 2009/0158504 A1 | 6/2009 | Sparrow et al. | |
| 2009/0282698 A1 * | 11/2009 | Kovacs | A43B 3/103 |
| | | | 36/28 |
| 2010/0005568 A1 * | 1/2010 | Smith | D02G 3/328 |
| | | | 66/178 R |
| 2011/0191942 A1 | 8/2011 | Villalobos | |
| 2011/0277218 A1 | 11/2011 | Padilla et al. | |
| 2011/0302699 A1 * | 12/2011 | Kaneda | D04B 1/26 |
| | | | 2/239 |
| 2012/0167276 A1 | 7/2012 | Brosie et al. | |
| 2012/0324961 A1 | 12/2012 | Clemendot | |
| 2013/0233025 A1 * | 9/2013 | Ishida | D02G 3/32 |
| | | | 66/187 |
| 2014/0304895 A1 | 10/2014 | Stuart | |
| 2014/0311181 A1 | 10/2014 | Amarasiriwardena et al. | |
| 2015/0033447 A1 | 2/2015 | Riaz | |
| 2015/0264995 A1 | 9/2015 | Hilderbrand, IV | |
| 2016/0024692 A1 * | 1/2016 | Yung | D03D 15/56 |
| | | | 139/421 |
| 2016/0120233 A1 | 5/2016 | Van Tiel et al. | |
| 2016/0278442 A1 | 9/2016 | Moran | |
| 2016/0340813 A1 | 11/2016 | Amis et al. | |
| 2017/0000216 A1 | 1/2017 | Dua et al. | |
| 2017/0035120 A1 | 2/2017 | Ramsey et al. | |
| 2017/0071264 A1 * | 3/2017 | Towfigh | A41C 1/10 |
| 2017/0143525 A1 * | 5/2017 | Matfus | A41D 31/18 |
| 2017/0216058 A1 | 8/2017 | Dias et al. | |
| 2017/0273363 A1 | 9/2017 | Patchin et al. | |
| 2017/0295851 A1 | 10/2017 | Thibodeau | |
| 2017/0311650 A1 | 11/2017 | Hupperets et al. | |
| 2018/0207035 A1 | 7/2018 | Gaither et al. | |
| 2019/0029331 A1 | 1/2019 | Field | |
| 2019/0037967 A1 | 2/2019 | Mcfarland et al. | |
| 2019/0104780 A1 | 4/2019 | Pinto Rodrigues | |
| 2019/0127895 A1 * | 5/2019 | Cheng | D04B 1/10 |
| 2019/0345651 A1 * | 11/2019 | Liang | A61F 13/08 |
| 2020/0080242 A1 | 3/2020 | Dardinski et al. | |
| 2020/0100920 A1 | 4/2020 | Finke | |

(56) References Cited

U.S. PATENT DOCUMENTS

| | | | |
|---|---|---|---|
| 2020/0179140 | A1 | 6/2020 | Valois et al. |
| 2020/0205484 | A1 | 7/2020 | Yehuda |
| 2020/0221791 | A1* | 7/2020 | Gazit .................. A41B 11/008 |
| 2020/0297514 | A1 | 9/2020 | Prescott et al. |
| 2020/0308738 | A1 | 10/2020 | Lineberry et al. |
| 2020/0347530 | A1 | 11/2020 | Tannebaum |
| 2021/0068471 | A1 | 3/2021 | Giorgi et al. |
| 2021/0071329 | A1 | 3/2021 | Cummings |
| 2022/0256963 | A1 | 8/2022 | Dekovic et al. |

FOREIGN PATENT DOCUMENTS

| | | |
|---|---|---|
| CN | 110352018 A | 10/2019 |
| CN | 209995385 U | 1/2020 |
| DE | 2719578 A1 | 5/1978 |
| DE | 20219015 U1 | 4/2003 |
| EP | 2815728 B1 | 1/2016 |
| EP | 3081680 A1 | 10/2016 |
| EP | 3330419 A1 | 6/2018 |
| FR | 2879405 B1 | 4/2007 |
| GB | 2271923 A | 5/1994 |
| JP | 09273005 A * | 10/1997 |
| JP | 11140702 A * | 5/1999 ............. A41B 11/02 |
| JP | 2007-239129 A | 9/2007 |
| JP | 2009-97122 A | 5/2009 |
| WO | 2004/052132 A1 | 6/2004 |
| WO | 2007/031790 A2 | 3/2007 |
| WO | 2012/006654 A1 | 1/2012 |
| WO | 2012/160834 A1 | 11/2012 |
| WO | WO-2017112926 A1 * | 6/2017 |
| WO | 2018/226194 A1 | 12/2018 |
| WO | 2019/028347 A1 | 2/2019 |
| WO | 2020/149951 A1 | 7/2020 |

OTHER PUBLICATIONS

International Search Report and Written Opinion received for PCT Patent Application No. PCT/US2021/059939, mailed on May 6, 2022, 21 pages.
1 Non-Final Office Action received for U.S. Appl. No. 17/525,623, mailed on Oct. 6, 2022, 9 pages.
International Preliminary Report on Patentability received for PCT Patent Application No. PCT/US2021/059928 mailed on Jul. 13, 2023, 12 pages.
International Preliminary Report on Patentability received for PCT Patent Application No. PCT/US2021/059939 mailed on Jul. 13, 2023, 13 pages.
Notice of Allowance Received for U.S. Appl. No. 17/525,623, mailed on Aug. 9, 2023, 5 pages.
International Preliminary Report on Patentability received for PCT Patent Application No. PCT/US2021/059920, mailed on Feb. 7, 2023, 9 pages.
2 Non-Final Office Action received for U.S. Appl. No. 17/525,640, mailed on Feb. 28, 2023, 17 pages.
1 Final Office Action received for U.S. Appl. No. 17/525,623, mailed on Mar. 27, 2023, 9 Pages.
Notice of Allowance received for U.S. Appl. No. 17/525,640, mailed on Sep. 7, 2023, 12 pages.
A/K Brim Sheath, Knit-Rite, knitrite.com, Available online at: <http://www.knitrite.com/prosthetics/sheaths/brimsheath.html>, Nov. 2, 2012, 2 pages.
Above-Knee Amputee Prosthetic Brim Sheath by GlideWear. Protects Skin from Irritation, Rubbing, Pain, GlideWear, amazon.com, ASIN: B01A5U0G2Q, Nov. 25, 2020, 4 pages.
Ez Sox Toddler Boys Socks Non Skid Anti Slip Grip Seamless Toe Pull Up Loops, Ez Sox, Amazon, ASIN: B01HPAA3G8, Available online at: <https://www.amazon.com/Ez-Sox-Toddler-Boys-Seamless/dp/B01HPAA3G8>, Accessed on Apr. 11, 2019, pp. 1-9.
Five Things to Know About Nike's New NBA Socks, Nike News, nike.com, Available on Internet at: <https://news.nike.com/news/nba-socks>, Sep. 15, 2017, 11 pages.
Guardian Liner, ALPS&trade, Available online at: <https://easyliner.jp/wp-content/uploads/2018/09/Guardian-Liner_EN.pdf>, Nov. 25, 2020, 2 pages.
Home: TRUSOX®—Performance Enhancing Socks, Trusox, trusox.com, Available on Internet at: <https:// web.archive.org/web/20130814050226/http://www.trusox.com>, Aug. 14, 2013, 2 pages.
Liner—Cushion Smart Seal—Above Knee, ALPS™, amputeedepot.com, Available online at: <https://amputeedepot.com/products/alps-smart-seal-cushion-liner-above-knee>, Nov. 25, 2020, 5 pages.
Ronnox Women's Cushioned Anti-Skid Non-Slip Silicone-Gripper Socks, For Yoga Pilales & Barre (Fits Women's Shoe Size 8-14), Amazon, amazon.com, ASIN: B071W2JXXR, Available on Internet at <htlps://www.amazon.com/dp/B071W2JX XR>, Oct. 26, 2017, 5 pages.
Socks With Loops, Active Hands, Available online at: <https://www.activehands.com/product/socks-with-loops/>, Accessed on Apr. 11, 2019, pp. 1-4.
Stella McCartney: Black Loop Sock Sneakers, SSense, 191471F127002, Available online at: <ssense.com>, Accessed on Apr. 11, 2019, pp. 1-6.
ToeSox—Low Rise Grip Socks, T8 Fitness, Available online at: <https://www.t8fitness.com/products/toesox-low-rise-grip-socks>, Accessed on Apr. 11, 2019, pp. 1-2.
Valor Amputee Sock—Below Knee Mid-Volume, Swiftwick, atlantacycling.com, Available online at: <https://www.atlantacycling.com/product/swiftwick-valor-amputee-sock-below-knee-mid-volume-302001-1.htm>, Nov. 25, 2020, 3 pages.
International Search Report and Written Opinion for PCT application No. PCT/US2021/059928, mailed on Feb. 25, 2022, 19 pages.
International Search Report and Written Opinion received for PCT Patent Application No. PCT/US2021/059920, mailed on Feb. 22, 2022, 16 pages.
Invitation to Pay Additional Fees received for PCT Patent Application No. PCT/US2021/059939, mailed on Mar. 14, 2022, 15 pages.

* cited by examiner

SLEEVE FOR AN EXTREMITY

CROSS-REFERENCE TO RELATED APPLICATIONS

This application claims the benefit of priority of U.S. App. No. 63/132,593, filed Dec. 31, 2020, and titled, "Sleeve for an Extremity," U.S. App. No. 63/164,677, filed Mar. 23, 2021, and titled "Knit Article with Variable Features," and U.S. App. No. 63/157,890, filed Mar. 8, 2021, and titled "Athletic Sock." The entireties of the aforementioned applications are incorporated by reference herein.

TECHNICAL FIELD

Aspects herein relate to a tubular knit sleeve for a below-the-knee amputee.

BACKGROUND

Prosthetic liners or sleeves are used to cover the residual limb of a below-the-knee amputee and act as an interface between a prosthetic leg and a wearer's skin surface helping to protect the wearer's skin from irritation. Such liners are typically made from silicone, thermoplastic elastomers, polyurethane, neoprene, and the like. These liners may lack features that make them suitable for standalone wear (wear without a prosthetic leg) during, for example, athletic activities. For example, some below-the-knee amputees choose to participate in sports without using a prosthetic leg(s); one such sport is wrestling. In these instances, traditional prosthetic liners may not include features such as zoned breathability, zoned cushioning, zoned grip, and zoned traction that maximize the wearer's athletic performance when participating in a particular sport.

BRIEF DESCRIPTION OF THE DRAWINGS

Examples of aspects herein are described in detail below with reference to the attached drawings figures, wherein.

DETAILED DESCRIPTION

Figure 1:
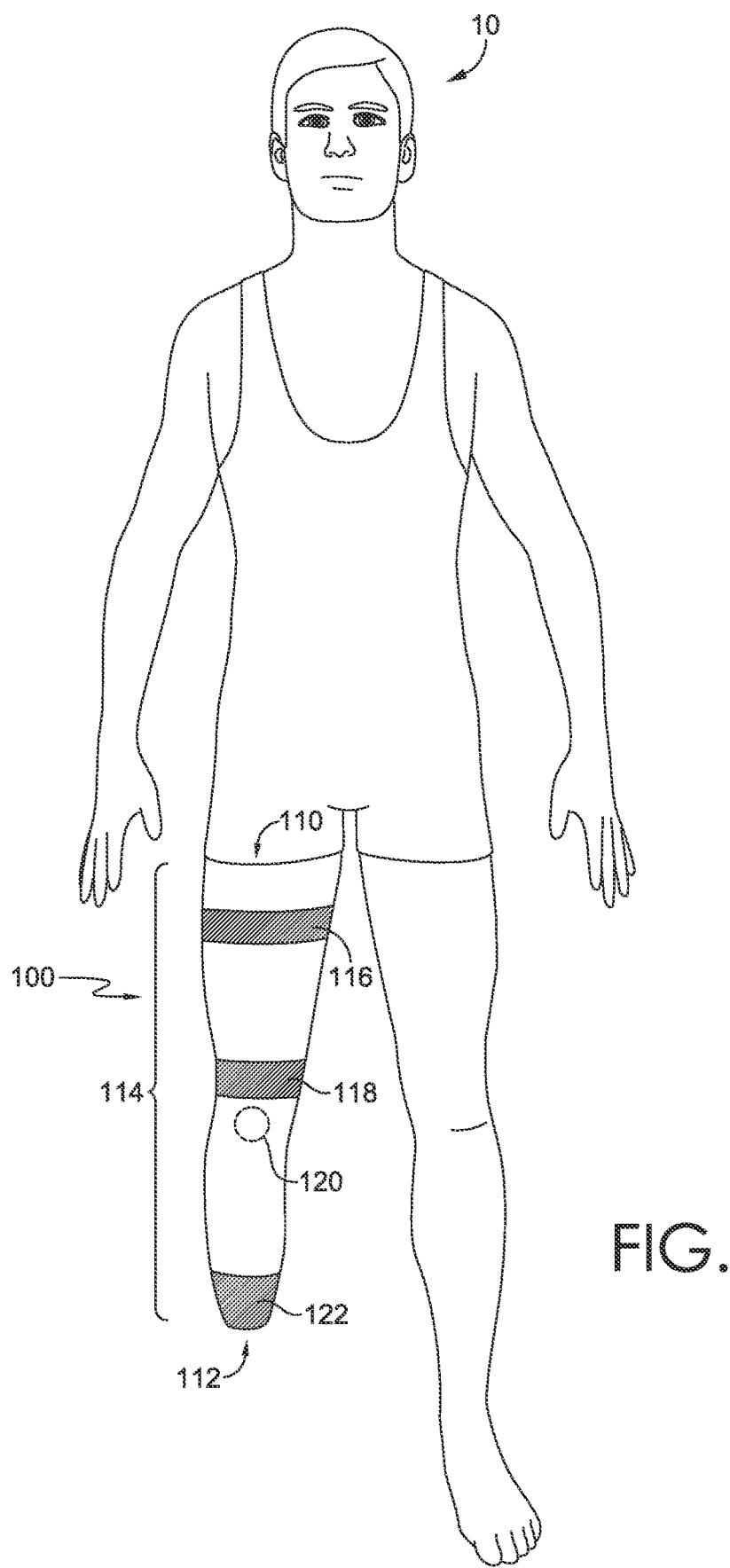
FIG. 1 illustrates a front view of a wearer standing upright and wearing an example tubular knit sleeve in accordance with aspects herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Traditional prosthetic liners or sleeves are used to cover the residual limb of a below-the-knee amputee and act as an interface between a prosthetic leg and a wearer's skin surface helping to protect the wearer's skin from irritation. Such liners are typically made from silicone, thermoplastic elastomers, polyurethane, neoprene, and the like. These liners may lack features that make them suitable for standalone wear (wear without a prosthetic leg) during, for example, athletic activities. For example, some below-the-knee amputees choose to participate in sports without using a prosthetic leg(s); one such sport is wrestling. In these instances, traditional prosthetic liners may not include features such as zoned breathability, zoned cushioning, zoned grip, and zoned traction that maximize the wearer's athletic performance.

Aspects herein are directed to a tubular knit sleeve for a residual limb of a below-the-knee amputee where the knit sleeve is designed for standalone wear during, for example, athletic activities such as wrestling. Features of the knit sleeve as described below may be applied to knit sleeves for residual limbs of other types of amputees such as those who have undergone, for example, ankle disarticulation, hand and wrist disarticulation, below-elbow amputation, above-elbow amputation, elbow disarticulation, and the like and may be tailored to maximize athletic performance in particular sports that utilize the residual limb. Moreover, features of the knit sleeve may also be applied to other types of sleeves and article of apparel, including socks, meant to be worn on a wearer's extremity.

The tubular knit sleeve, in accordance with aspects herein, has an open first end, a closed second end, and a tubular body extending between the first end and the second end; the knit sleeve is configured to be worn over a residual limb of a below-the-knee amputee either alone or with a liner positioned between the knit sleeve and the residual limb. The first end of the knit sleeve is configured to be generally positioned around the upper thigh of the wearer and the second end is configured to fit snugly around the lower end of the residual limb. In example aspects, the knit sleeve includes zoned grip features that help to maintain the sleeve in a relatively fixed position during wearer movement including movements used when wrestling. For example, the knit sleeve includes a number of knit-in grip bands that are knit with grip yarns, such as a welt grip band, an upper grip band, and a middle grip band. These grip bands are positioned at locations along the length of the tubular body and extend entirely around a circumference of the knit sleeve to provide 360-degree grip. The grip bands may help prevent the knit sleeve from, for example, sliding downward or rotating during wear. The grip bands may also include a lower grip band that extends partially around the circumference of the knit sleeve. The lower grip band may be positioned on the back of the knit sleeve adjacent to the second end. The front of the knit sleeve in this location may be subject to forward, backward, and rotational forces during wrestling movements, and the location of this lower grip band may help to minimize rotation or movement of the knit sleeve during wear thus reducing chances of skin irritation.

The tubular knit sleeve may further include a reinforcement zone located on the front aspect of the knit sleeve in an area corresponding to below the knee of the wearer to the end or near the end of the residual limb when the knit sleeve is worn. During wrestling movements, this area of the wearer may be positioned on the wrestling mat and may experience high acceleration forces as the wrestling shoots his upper body forward or is pushed back by an opponent. To help provide traction and prevent slippage, the reinforcement zone may be knit using thermoplastic polyurethane (TPU) yarns, and in example aspects, a TPU material may be deposited on the TPU yarns to create a chemical bond as well as a mechanical bond between the two such that the TPU material is firmly adhered to the TPU yarns. The TPU material, in example aspects, is applied in a pattern that generates maximum traction when forward and backward forces are applied to this area helping to provide a secure base for the wrestler. For example, the TPU material may be deposited in a plurality of linear segments that are oriented orthogonal to a longitudinal axis that extends between the first end and the second end of the knit sleeve. This deposition pattern presents a large contact area when forward and backward forces (i.e., forces that are orthogonal to the linear segments) are applied to the reinforcement zone helping to provide a secure base and minimizing chances of slipping.

The tubular knit sleeve may also include zoned cushioning features and zoned breathability features. For example, the area of the knit sleeve located between the upper and middle grip band is knit in a mesh pattern to facilitate permeability and breathability. This area is configured to be located at an upper thigh area of the wearer when the knit sleeve is worn. At least the middle grip band and the lower grip band may be knit with terry loops facing toward a skin surface of the wearer to provide cushioning and additional surface area for gripping. As well, the reinforcement zone, which is generally in contact with the ground when the wrestler is wrestling may also be knit with terry loops to provide cushioning at this contact surface. The lower back of the knit sleeve, which is configured to be located at a calf area of the wearer is knit in a mesh pattern to facilitate air permeability and breathability.

In example aspects, the second end of the knit sleeve may include a knit structure that increases compression in this area to provide a snug fit around the end of the residual limb. For instance, the knit structure may include a repeating pattern that has a first number of knit courses of a body yarn and a plating yarn knit in a basic knit stitch with terry loops followed by a second number of knit courses where the body yarn is floated for a first number of stitches and knit for a second number of stitches; the second number of knit courses are integrally knit with the first number of knit courses. Floating the body yarn increases stretch resistance and increases the allover compression at the second end of the knit sleeve. In example aspects, the second end of the knit sleeve may also taper inwardly to conform more closely to the anatomy of the end of the wearer's residual limb.

Aspects herein contemplate that the knit sleeve may optionally be worn with a tubular knit liner where the liner is configured to be positioned between the knit sleeve and the residual limb. The knit liner includes an open first end, a closed second end, and a tubular body extending between the first end and the second end. Like the knit sleeve, the liner may also include zoned breathability features, zoned cushioning features, and zoned grip features. For example, the liner may include a welt grip band knit with grip yarns, where the welt grip band extends around the circumference of the liner and helps to secure the liner around an upper thigh area of the wearer. The liner may include additional leg bands, such as a middle leg band and a lower leg band that are knit with, for example, elastic yarns and further help to secure the liner against the wearer's residual limb through additional compression. The tubular knit liner may also include a mesh knit structure in the upper and lower part of the tubular body to provide breathability and permeability. Similar to the second end of the knit sleeve, the second end of the liner may also be knit with the knit structure described above (e.g., a repeating pattern of courses knit with a basic knit stitch with terry loops and courses where the body yarn is knit for a first number of knit stitches and floated for a second number of knit stitches) to provide cushioning and compression at the end of the residual limb. Like the tubular knit sleeve, the second end of the knit liner may also taper inwardly to conform more closely to the anatomy of the end of the wearer's residual limb.

The term "tubular knit sleeve" or "knit sleeve" as used herein refers to a tubular body having a first end and a second end that is configured to be worn over an extremity or a residual limb of a wearer. In example aspects, the first end of the knit sleeve may be open such that the wearer can draw the knit sleeve over the extremity or residual limb. Aspect herein contemplate that the second end may be open or closed. The knit sleeve has a length extending between the first end and the second end, and a circumference that extends around the tubular body. Positional terms as used herein to describe the knit sleeve are with respect to the knit sleeve being worn by a wearer standing in an upright position with the residual limb in an extended position (i.e., the knee straight). In this aspect, the first end of the knit sleeve is located superior to the second end of the knit sleeve. Thus, the positional term "upper" when describing the knit sleeve means located closer to the first end, and the term "lower" means located closer to the second end. The term "middle" means located approximately midway between the first end and the second end. The term "inner-facing surface" means the surface that faces toward a skin or body surface of a wearer, and the term "outer-facing surface" means the surface that faces away from the inner-facing surface and toward an external environment. The term "front" or "front aspect" when describing the knit sleeve means the portion of the knit sleeve that is configured to cover the front of an upper thigh area, a knee area, and part of the shin area of the wearer, and the term "back" or "back aspect" means the portion of the knit sleeve that is configured to cover the back of the upper thigh area, the back of the knee area, and part of the calf area of the wearer. The term "longitudinal axis" as used herein refers to an axis that extends between the first end and the second end when the knit sleeve is being worn as described above (a wearer standing upright with the residual limb extended). The same terminology may be applied to the tubular knit liner as described herein.

The term "grip yarns" used when describing yarns that form the grip bands refer to a yarn having a high number of filaments (e.g., 7000 or greater) per single yarn strand such that the denier per filament of the grip yarn is about 0.01 or less. In example aspects, the grip yarn may be formed through an "islands-in-the-sea" process. An example filament that may be used in the grip yarn is NANOFRONT® produced by Teijin Limited with headquarters in Tokyo, Japan. An example grip yarn may comprise three strands of a 145 decitex grip yarn. In example aspects, the grip yarn may include an additional yarn. For instance, the grip yarn may cover a nylon yarn for added bulk in some example aspects. The large number of filaments provides a large surface-to-volume ratio for the yarn, which contributes to the gripping function of the yarn. To describe it differently, the large number of filaments within the yarn causes the yarn to have a higher coefficient of friction as compared to, for example, more typical yarns that incorporate a smaller number of filaments within a single yarn strand such as yarns that incorporate from between, for example, 50 filaments to 500 filaments per yarn. The term "elastic yarn" as used herein refers to the yarn's ability to stretch from about 100% to about 200% of its original length and recover to approximately its original length after the stretching force is removed.

The term "knit course" as used herein refers to a predominantly horizontal row of knit loops (in an upright textile as knit) that are produced by adjacent needles during the same knitting cycle. The knit course may comprise one or more stitch types such as a knit stitch, a held stitch, a float stitch, a tuck stitch, a transfer stitch, and the like as these terms are known in the art of knitting. The term "knit stitch" or "basic knit stitch" as used herein refers to the basic stitch type where the yarn is cleared from the needle after pulling a loop of the yarn from the back to the front of the textile through a previous stitch. Thus, the legs of the stitch appear on the technical face of the knit textile and the top and bottom of the stitch appear on the technical back of the textile. The term "wale" as used herein is a predominantly vertical column of intermeshed or interlooped knit loops, generally produced by the same needle at successive (but not necessarily all) courses or knitting cycles. The terms "horizontal" and "vertical" as used herein are relative to an upright textile as knit in which the heads of knit loops face toward the top of the textile and the course knit first is oriented toward the bottom of the textile.

The term "float stitch" as used herein occurs when no new stitch is formed at a needle. Thus, the float yarn may extend across one or more adjacent wales. The term "plating" as used herein means a knit construction where one or more body yarns and one or more plating yarns are knit in the same knit stitch using, for instance, a body yarn feeder and one or more plating yarn feeders. The term "terry loops" as used herein refers to loops formed from knit yarns that extend away from the technical face and/or the technical back of a knit textile and is to be given the meaning that is commonly used in the knitting art space. In example aspects, the terry loops extend away from the technical back of the knit sleeve and/or knit liner, where the technical back forms the inner-facing surface of the knit sleeve and/or knit liner.

The term "integrally knit" as used herein means a textile or fabric having a yarn from one or more knit courses being interlooped with one or more knit courses of another area. For instance, a knit course from a first area of the knit sleeve may be integrally knit with a knit course from a second area of the knit sleeve if a yarn from the first area is interlooped with a knit course in the second area. It is contemplated herein that the knit sleeve and the knit liner are each integrally knit.

Unless otherwise noted, all measurements provided herein are measured at standard ambient temperature and pressure (25 degrees Celsius or 298.15 K and 1 bar) with the knit sleeve or knit liner in a resting or non-tensioned state. The term "about" as used herein means within ±10% of an indicated value.

FIG. 1 illustrates a front view of a wearer 10 with a below-the knee amputation wearing a tubular knit sleeve 100. Although the wearer 10 is shown having a single below-the-knee amputation, it is contemplated herein that the wearer 10 may be a double below-the-knee amputee. In this instance, the wearer 10 may utilize two knit sleeves as described herein. A front aspect of the knit sleeve 100 is depicted. The knit sleeve 100 includes an open first end 110, a closed second end 112, and a tubular body 114 extending between the first end 110 and the second end 112. The term "end" when used to describe the first end 110 and the second end 112 generally means the area adjacent to and including the terminal end of the knit sleeve 100. The first end 110 of the knit sleeve 100 is configured to encircle an upper thigh area of the wearer 10, and the second end 112 is configured to enclose the end of the wearer's residual limb.

The knit sleeve 100 includes an upper grip band 116 positioned adjacent to the first end 110 of the knit sleeve 100. As such, the upper grip band 116 helps to secure the knit sleeve 100 around the upper thigh of the wearer 10. The knit sleeve 100 further includes a middle grip band 118 that is configured to be positioned superior to the wearer's knee, which is indicated by reference numeral 120. The middle grip band 118 further helps to secure the knit sleeve 100 in position and reduces the chances of the knit sleeve 100 sliding downwards and/or rotating. The knit sleeve 100 additionally includes a knit structure 122 located at the second end 112 of the knit sleeve 100. As explained further below, the knit structure 122 facilitates the second end 112 fitting snugly around the end of the residual limb of the wearer 10.

Figure 2:
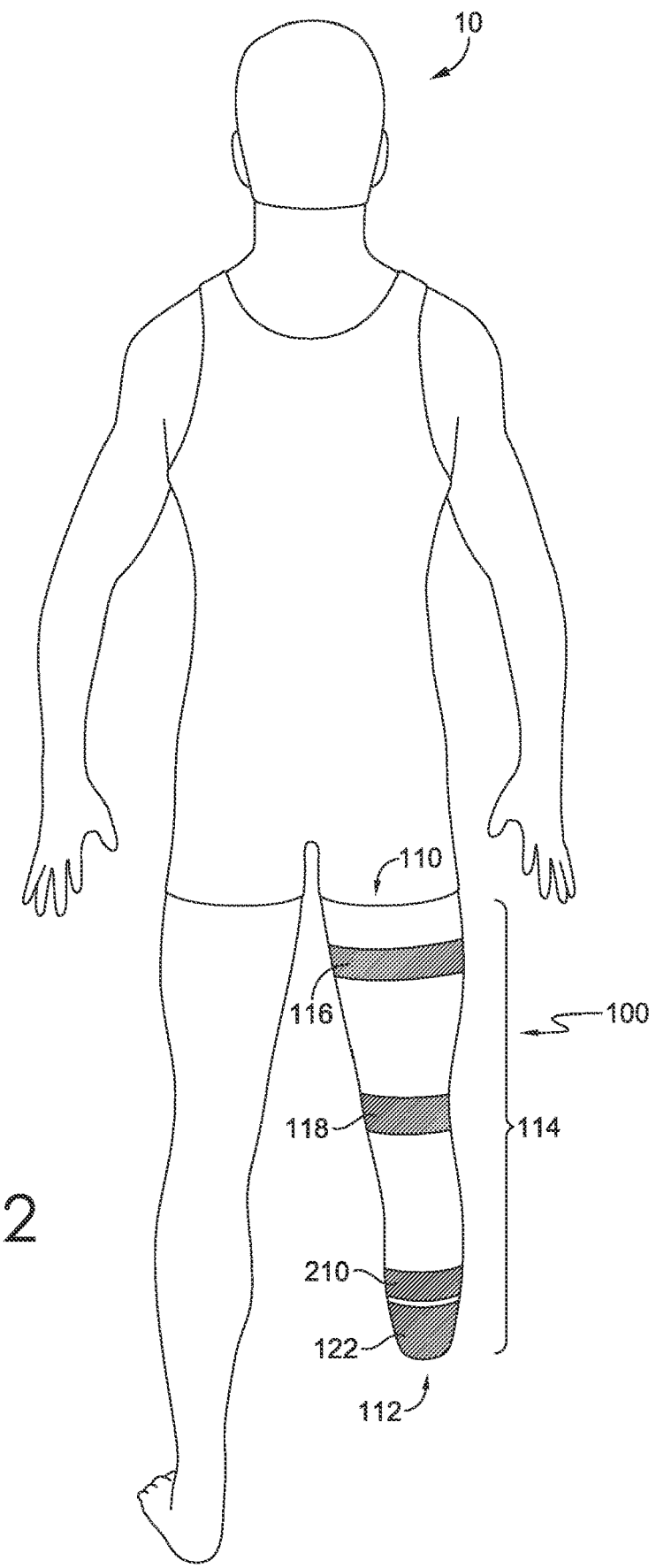
FIG. 2 illustrates a back view of the wearer standing upright and wearing the example tubular knit sleeve in accordance with aspects herein.

FIG. 2 illustrates a back view of the wearer 10. A back aspect of the knit sleeve 100 is depicted. The upper grip band 116 and the middle grip band 118 are shown encircling the circumference of the knit sleeve 100 and the thigh of the wearer 10. The knit structure 122 is also shown covering the back of the end of the residual limb of the wearer 10. FIG. 2 further depicts a lower grip band 210 that is positioned just on the back aspect of the knit sleeve 100. The lower grip band 210 is configured to be positioned adjacent to an upper calf area of the wearer 10 and helps to prevent the knit sleeve 100 from rotating especially when traction forces are applied to the front of the knit sleeve 100 thus reducing the chances of skin irritation.

Figure 3:
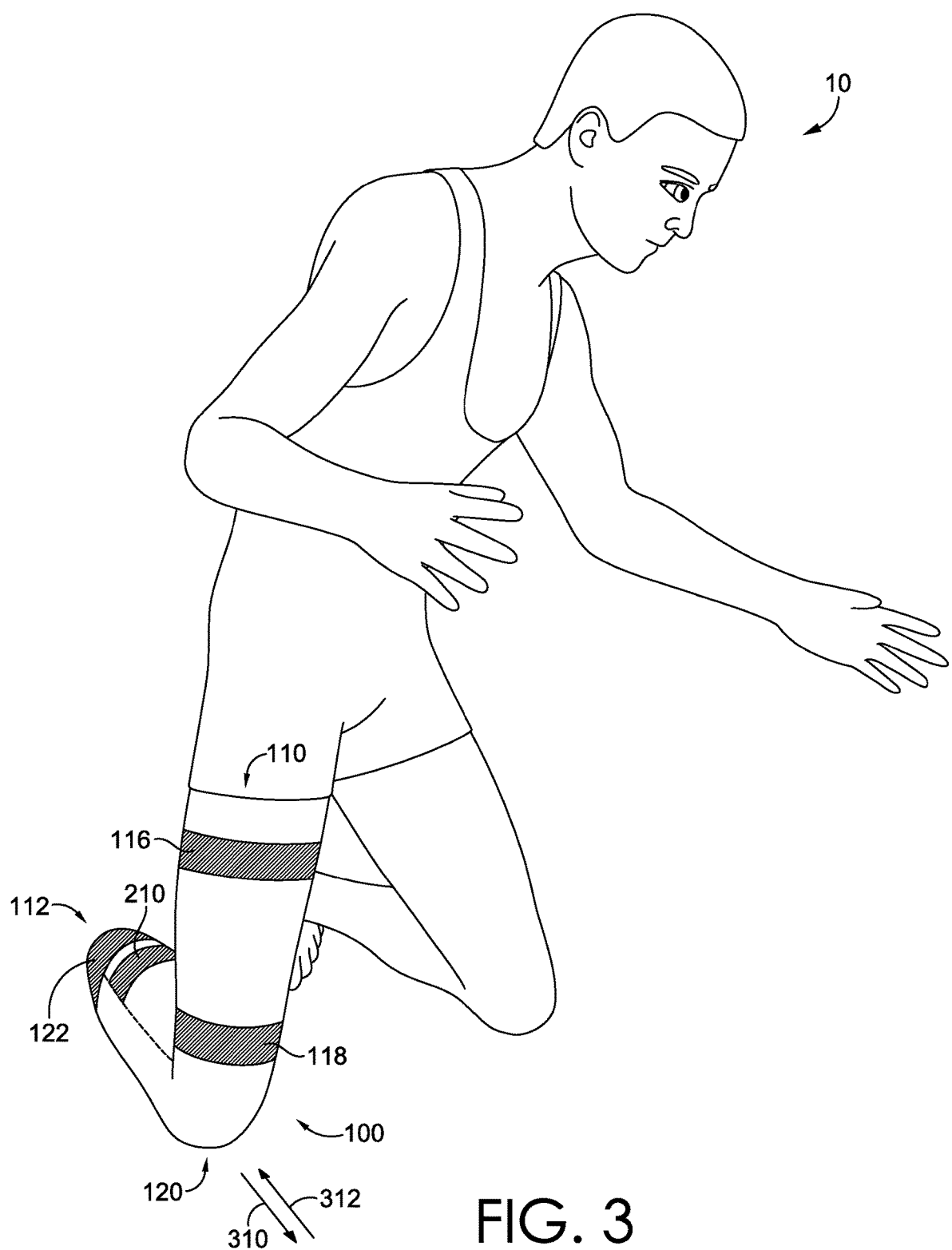
FIG. 3 illustrates the wearer in a wrestling position and wearing the example tubular knit sleeve in accordance with aspects herein.

FIG. 3 illustrates the wearer 10 in an example wrestling stance. As shown, the front portion of the wearer's residual limb located below the wearer's knee is positioned in contact with a ground surface such as a wrestling mat. This corresponds to the area of the knit sleeve 100 below the middle grip band 118, known herein as a reinforcement zone. The reinforcement zone thus acts as the primary contact area for the wrestler when shooting forward, when rotating, or when being pushed back by an opponent. For the wearer 10, the bending joint closest to the ground surface is the wearer's knee 120, which generally exhibits movement through one axis of rotation. This differs from wrestlers with intact limbs where the bending joint closest to the ground surface is the ankle joint, which generally exhibits motion through multiple different axes of rotation. Because the wearer 10 is closer to the ground surface, he has a lower center of gravity compared to wrestlers with intact limbs. Thus, the wearer 10 is able to achieve a greater change in applied force angle to the ground without as much upper body lean resulting in a quicker force application to the reinforcement zone. A quicker force application, in turn, may increase the chances of slipping in this area. Moreover, the forces generated by the large thigh, hip, and gluteal muscles of the wearer 10 are transferred through the wearer's knee with its one axis of rotation directly to the front portion of the wearer's residual limb located below the wearer's knee instead of being transferred through the calves, ankles, and feet of a wrestler with intact limbs. This also contributes to a quicker force application to the reinforcement zone. As explained further below, to minimize the chances of slipping and to allow for quick acceleration of the wearer's body, the knit sleeve 100 is constructed to have increased traction in the reinforcement zone. The increased traction provides for a stable base when the wearer 10 is shooting forward as indicated by direction arrow 310 or when the wearer 10 is being pushed backward as indicated by direction arrow 312.

Figures 4, 5:
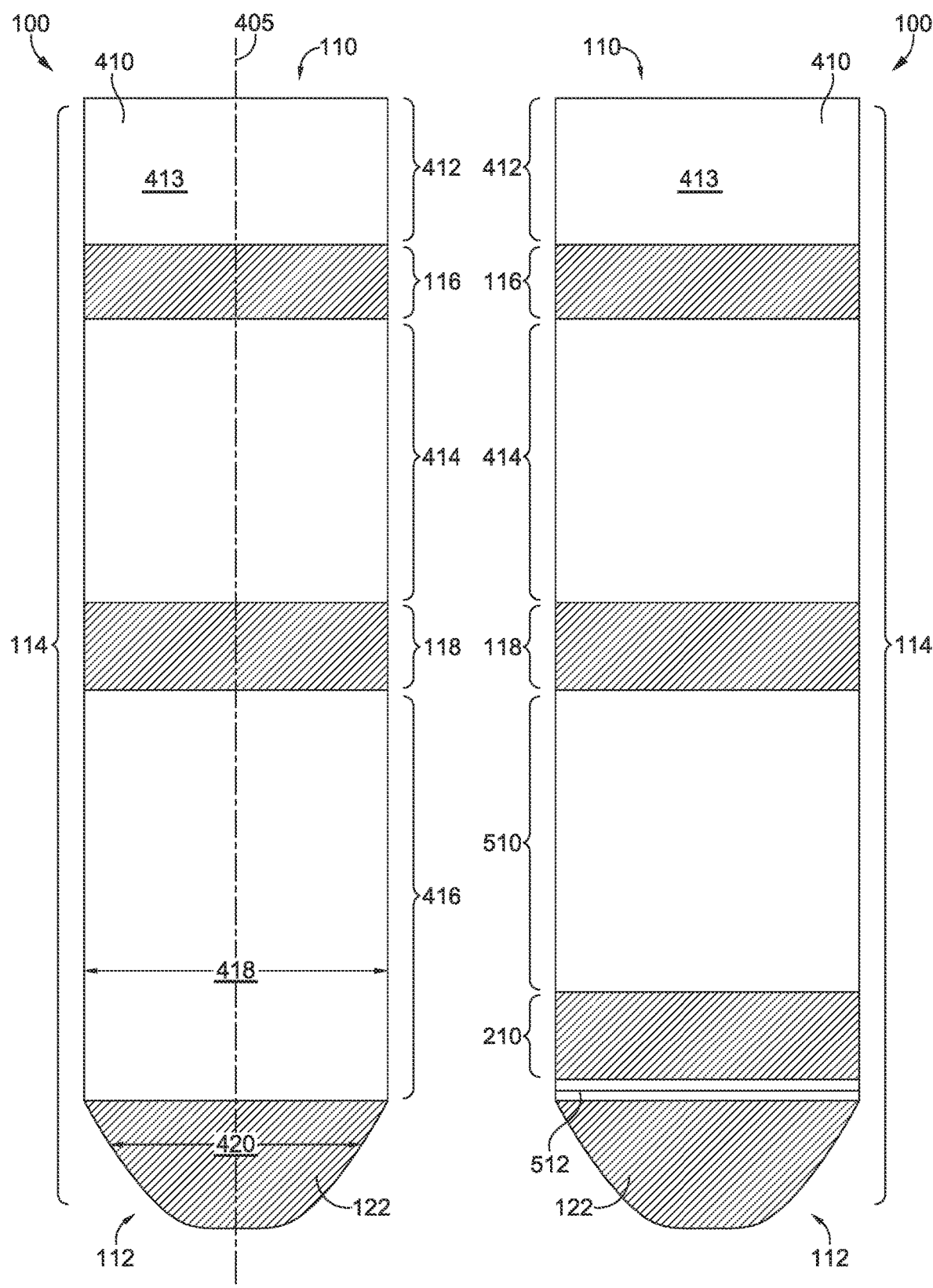
FIG. 4 illustrates a front view of the example tubular knit sleeve and depicts an outer-facing surface of the tubular knit sleeve in accordance with aspects herein.
FIG. 5 illustrates a back view of the example tubular knit sleeve of FIG. 4 in accordance with aspects herein.

FIG. 4 depicts the front aspect of an outer-facing surface 410 of the knit sleeve 100 where the knit sleeve 100 is depicted as lying flat. Reference numeral 405 indicates a theoretical axis that extends longitudinally from the first end 110 to the second end 112 of the knit sleeve 100. In example aspects, the overall length of the knit sleeve 100 as measured from the terminal end of the first end 110 to the terminal end of the second end 112 may be from about 40 cm to about 48 cm, from about 41 cm to about 47 cm, from about 42 cm to about 46 cm, from about 43 cm to about 45 cm, or about 44 cm.

The knit sleeve 100 includes a welt zone 412 located between the first end 110 and the upper grip band 116. In example aspects, the welt zone 412 may be a double-layered structure that includes an exterior welt layer 413, as depicted in FIG. 4 that forms part of the outer-facing surface 410 of the knit sleeve 100 and an interior welt layer that will be discussed with respect to FIGS. 7A and 8. The interior welt layer is integrally knitted with the exterior welt layer 413 and is formed by folding the interior welt layer inwardly from the exterior welt layer 413 to form the double-layered welt zone 412. In example aspects, the exterior welt layer 413 may comprise a single jersey knit structure knit with a body yarn and a plating yarn. In example aspects, the body yarn may comprise a polyester yarn. For example, the body yarn may comprise four strands of a 167 decitex polyester yarn. The plating yarn may comprise an elastic yarn covered with a nylon yarn. For example, the plating yarn may comprise a 78 decitex spandex yarn single covered by two strands of 78 decitex nylon. In example aspects, the welt zone 412 may have a width as measured from the first end 110 to a lower edge of the welt zone 412 (or upper edge of the upper grip band 116) from about 5 cm to about 8 cm, from about 5.5 cm to about 7.5 cm, from about 6 cm to about 7 cm, or about 6.5 cm.

The upper grip band 116 is located immediately below the welt zone 412 and extends around the circumference of the tubular body 114. The upper grip band 116 may have a width as measured between its upper edge and its lower edge of from about 1.5 cm to about 3.5 cm, from about 2 cm to about 3 cm, or about 2.5 cm. In example aspects, the upper grip band 116 may be knit using an upper set of grip yarns. For example, the body yarn used to knit the upper grip band 116 may comprise at least a grip yarn having a denier per filament of 0.01 or less, and the plating yarn used to knit the upper grip band 116 may comprise an elastic yarn that is covered with a nylon yarn. For example, the plating yarn may comprise a 78 decitex spandex yarn single covered with two strands of 78 decitex nylon. It is contemplated herein that an additional yarn (e.g. an additional body yarn or an additional plating yarn) may be used in the upper grip band 116. For example, the additional yarn may include an elastic yarn covered with nylon such as a 33 decitex spandex yarn double covered with three strands of 78 decitex nylon. In example aspects, the upper grip band 116 may be knit as a single jersey knit structure. The use of grip yarns with their high surface-to-volume ratio, facilitates the upper grip band 116 securing the first end 110 of the knit sleeve 100 around the upper thigh area of a wearer.

An upper thigh zone 414 is located immediately below the upper grip band 116. In example aspects, the upper thigh zone 414 may comprise a mesh knit structure (a knit structure that includes knit-in holes) knit using a body yarn and a plating yarn. The use of a mesh knit structure promotes breathability and permeability in this area of the knit sleeve 100. In example aspects, the body yarn may comprise a polyester yarn. For example, the polyester yarn may comprise four strands of a 167 decitex polyester. The plating yarn may comprise an elastic yarn covered with a nylon yarn. For example, the plating yarn may comprise a 78 decitex spandex yarn single covered by two strands of 78 decitex nylon. In example aspects, the upper thigh zone 414 may have a width measured from its upper edge (or the lower edge of the upper grip band 116) to its lower edge (or the upper edge of the middle grip band 118) from about 10 cm to about 13 cm, from about 10.5 cm to about 12.5 cm, from about 11 cm to about 12 cm, or about 11.5 cm. The width of the upper thigh zone 414 is selected to substantially cover the wearer's thigh. Since this area is generally not in contact with the ground during a typical wrestling stance, breathability and permeability versus cushion is optimized.

The middle grip band 118 is located immediately below the upper thigh zone 414 and may have a width as measured between its upper edge and its lower edge of from about 2 cm to about 5 cm, from about 2.5 cm to about 4.5 cm, from about 3 cm to about 4 cm, or about 3.5 cm. In example aspects, the middle grip band 118 may be knit using a middle set of grip yarns. For example, the body yarn used to knit the middle grip band 118 may comprise at least a grip yarn having a denier per filament of 0.01 or less, and the plating yarn used to knit the middle grip band 118 may comprise an elastic yarn that is covered with a nylon yarn. For example, the plating yarn may comprise a 156 decitex spandex yarn single covered with two strands of 78 decitex nylon. It is contemplated herein that an additional yarn (e.g. an additional body yarn or an additional plating yarn) may be used in the middle grip band 118. For example, the additional yarn may include an elastic yarn covered with nylon such as a 33 decitex spandex yarn double covered with three strands of 78 decitex nylon. In example aspects, the middle grip band 118 may be knit as a single jersey knit structure with terry loops as explained further below with respect to FIGS. 7 and 8. Similar to the upper grip band 116, the use of grip yarns with their high surface-to-volume ratio and their high coefficient of friction, facilitates the middle grip band 118 securing the knit sleeve 100 around an area of the wearer directly above the wearer's knee.

A reinforcement zone 416 is located between the middle grip band 118 and the knit structure 122 located at the second end 112 of the knit sleeve 100. In example aspects, to provide a suitable substrate for deposition of a thermoplastic polyurethane (TPU) material, the reinforcement zone 416 may be knit with thermoplastic polyurethane (TPU) yarns where the TPU yarns are exposed on the outer-facing surface 410 of the knit sleeve 100. As explained further below, use of TPU yarns allows for both a chemical and a mechanical bonding between the deposited TPU material and the reinforcement zone 416. The reinforcement zone 416 may be knit as a single jersey knit structure with terry loops using, for instance, one strand of a 100 decitex TPU yarn in combination with a body yarn such as a polyester yarn. In example aspects, the polyester yarn may comprise four strands of 167 decitex polyester. The reinforcement zone 416, in example aspects, may have a width as measured between its upper end (or the lower edge of the middle grip band 118) and the upper edge of the knit structure 122 from about 14 cm to about 18 cm, from about 14.5 cm to about 17.5 cm, from about 15 cm to about 17 cm, from about 15.5 cm to about 16.5 cm, or about 16 cm.

The second end 112 of the knit sleeve 100 is located immediately below the reinforcement zone 416 and extends to the terminal end of the knit sleeve 100. The second end 112 is knit with the knit structure 122 that includes floats that provide an added amount of compression to the second end 112; the knit structure 122 is further described with respect to FIG. 10. In example aspects, the second end 112 may also be knit with grip yarns that add a gripping function. In further example aspects and as shown in FIG. 4, the second end 112 may be symmetrically tapered inwardly using a needle transfer process such that the tubular body 114 has a first width 418 as measured from a first side to a second side of the tubular body 114 above the second end 112 (e.g., in the reinforcement zone 416) and a second width 420 at the second end 112 where the second width 420 is less than the first width 418. The tapering shape of the second end 112 mimics the natural tapering of the end of the residual limb on the wearer. The use of the knit structure 122, the grip yarns, and the tapering of the second end 112 all contribute to providing a snug fit around the end of the wearer's residual limb helping to secure the knit sleeve 100 in place.

In addition to the grip yarns, the second end 112 may include an additional body yarn such as an elastic yarn covered with nylon. In one example aspect, the elastic yarn covered with nylon may comprise a 320 decitex spandex yarn single covered with four strands of 78 decitex nylon. The second end 112 may further include a plating yarn such as an elastic yarn covered by nylon. In one example aspect, the plating yarn may include a 156 decitex spandex yarn single covered with two strands of 78 decitex nylon. In example aspects, the second end 112 may have a width as measured from the lower edge of the reinforcement zone 416 to a terminal end of the second end 112 from about 2 cm to about 6 cm, from about 2.5 cm to about 5.5 cm, from about 3 cm to about 5 cm, from about 3.5 cm to about 4.5 cm, or about 4 cm.

FIG. 5 depicts the back aspect of the outer-facing surface 410 of the knit sleeve 100 where the knit sleeve 100 is depicted as lying flat. The back aspect includes the welt zone 412 and the exterior welt layer 413. As shown, the welt zone 412 extends circumferentially around the tubular body 114. The upper grip band 116 is also depicted and is shown extending circumferentially around the tubular body 114. In addition, the upper thigh zone 414 is shown extending around the circumference of the tubular body 114. The middle grip band 118 is further depicted as extending around the circumference of the tubular body 114.

The back aspect of the knit sleeve 100 includes a calf zone 510 located immediately below the middle grip band 118. In example aspects, the calf zone 510 comprises a mesh knit structure knit using a body yarn and a plating yarn. The use of a mesh knit structure promotes breathability and permeability in this area of the knit sleeve 100 which is generally not in contact with a ground surface. In example aspects, the body yarn may comprise a polyester yarn. For example, the polyester yarn may comprise four strands of a 167 decitex polyester. The plating yarn may comprise an elastic yarn covered with a nylon yarn. For example, the plating yarn may comprise a 156 decitex spandex yarn single covered by two strands of 78 decitex nylon. In example aspects, the calf zone 510 may have a width measured from its upper edge (or the lower edge of the middle grip band 118) to its lower edge (or the upper edge of the lower grip band 210) from about 9 cm to about 12 cm, from about 9.5 cm to about 11.5 cm, from about 10 cm to about 11 cm, or about 10.5 cm.

Immediately below the calf zone 510 is the lower grip band 210. The lower grip band 210 may have a width as measured between its upper edge and its lower edge of from about 1.5 cm to about 5 cm, from about 2 cm to about 4.5 cm, from about 2.5 cm to about 4 cm, or about 3 cm. In example aspects, the lower grip band 210 may be knit using a lower set of grip yarns. For example, the body yarn used to knit the lower grip band 210 may comprise at least a grip yarn having a denier per filament of 0.01 or less, and the plating yarn used to knit the lower grip band 210 may comprise an elastic yarn that is covered with a nylon yarn. For example, the plating yarn may comprise a 156 decitex spandex yarn single covered with two strands of 78 decitex nylon. It is contemplated herein that an additional yarn (e.g. an additional body yarn or an additional plating yarn) may be used in the lower grip band 210. For example, the additional yarn may include an elastic yarn covered with nylon such as a 33 decitex spandex yarn double covered with three strands of 78 decitex nylon. In example aspects, the lower grip band 210 may be knit as a single jersey knit structure with terry loops as explained further below with respect to FIGS. 7A and 8.

In example aspects, the lower grip band 210 is located just on the back aspect of the knit sleeve 100. Stated differently, in example aspects, the lower grip band 210 extends only partially around the circumference of the tubular body 114 and is absent on the front aspect of the knit sleeve 100. The location of the lower grip band 210 on an opposite side of the knit sleeve 100 from the reinforcement zone 416 and its use of grip yarns and terry loops facilitates the lower grip band 210 in helping to prevent the knit sleeve 100 from rotating especially when forces are applied to the reinforcement zone 416.

Between the lower grip band 210 and the second end 112 of the knit sleeve 100 is a seam 512 in example aspects. Positioning the seam 512 on the back aspect of the knit sleeve 100 as opposed to the front aspect or the terminal end of the second end 112 may reduce chaffing and/or irritation of the seam 512 since this location is generally not in contact with a ground surface. Moreover, this location instead of at the terminal end of the second end 112 may protective the sensitive skin of the end of the residual limb.

The knit structure 122 located at the second end 112 of the knit sleeve 100 is shown as further extending on to the back aspect of the knit sleeve 100 such that it provides 360 degree compression and gripping when the knit sleeve 100 is worn.

The description of the yarns used to knit the different zones and/or grip bands, the overall length of the knit sleeve 100, and the example widths for the different zones and/or grip bands are illustrative and it is contemplated herein that other types of yarns and other dimensions for the knit sleeve 100 and the different zones and/or grip bands may be utilized in accordance with aspects herein. With respect to the yarns used to knit the knit sleeve 100, for example, it is contemplated herein that additional yarns may be used. For example, it is contemplated that a laid-in yarn may be used in portions of the knit sleeve 100 to provide added reinforcement and structure. In one example aspect, the laid-in yarn may be used in all portions of the knit sleeve 100 except for in the knit structure 122. An example laid-in yarn may comprise an elastic yarn covered with nylon. For example, the laid-in yarn may comprise a 195 decitex LYCRA® yarn double covered with one strand of a 44 decitex nylon. With respect to the dimensions of the knit sleeve 100, the overall length of the knit sleeve 100 and the widths of the different zones and/or grip bands may be customized for a particular wearer using, for instance, body scan measurements as is known in the art. In other example aspects, the overall length of the knit sleeve 100 and the widths of the different zones and/or grip bands may be based on average measurements taken from a number of different wearers. Any and all aspects, and any combination thereof, are contemplated as being within aspects herein. It is further contemplated herein that the different grip bands such as the upper grip band 116, the middle grip band 118, and the lower grip band 210 may have a different visual property such as a different color than remaining portions of the knit sleeve 100 to provide an interesting visual aesthetic to the knit sleeve 100 and to provide a visual marker to the wearer to properly position the knit sleeve 100 on the wearer's residual limb.

Figure 6:
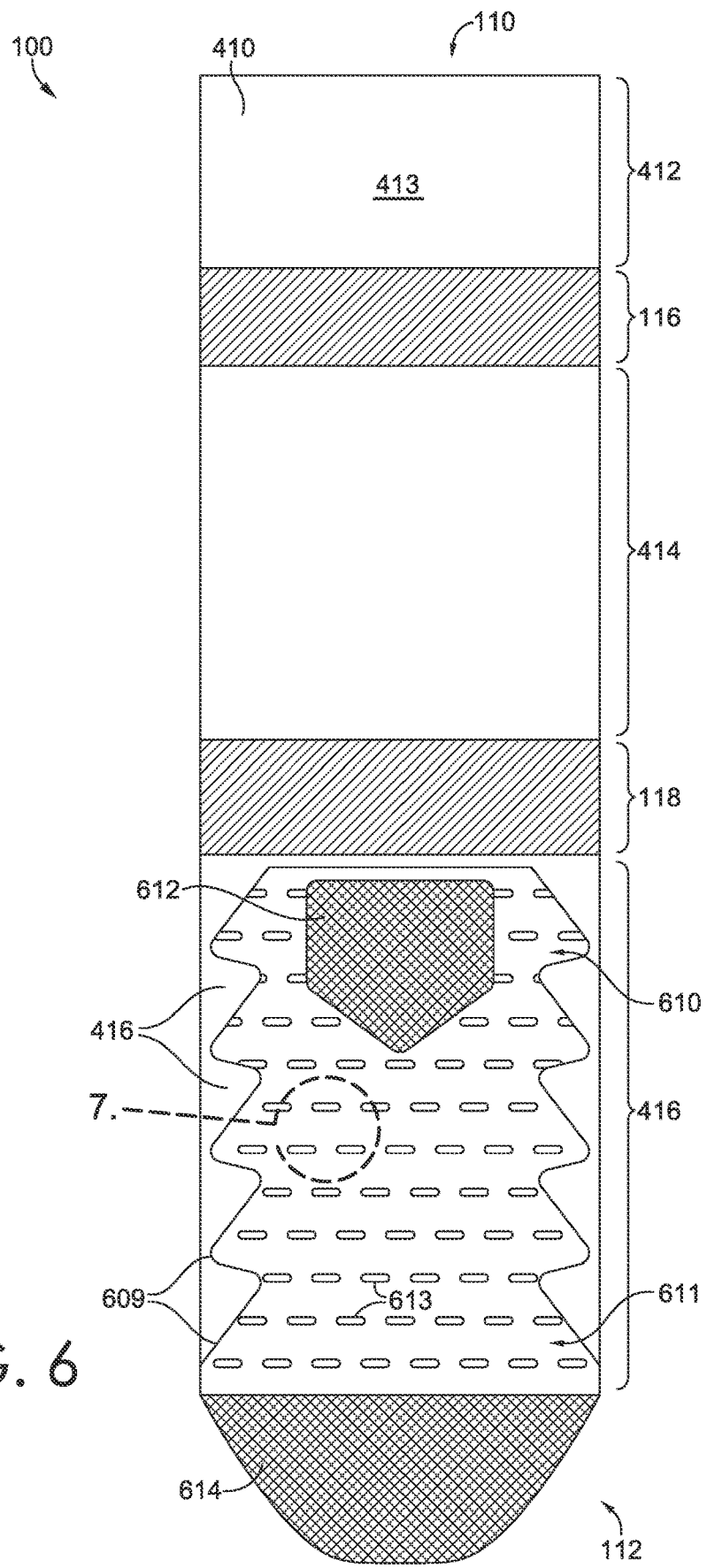
FIG. 6 illustrates a front view of the example tubular knit sleeve and depicts a thermoplastic polyurethane material deposited on an outer-facing surface of a reinforcement zone of the example tubular knit sleeve in accordance with aspects herein.

FIG. 6 illustrates the front aspect of the outer-facing surface 410 of the knit sleeve 100 with a TPU material 610 deposited on to the reinforcement zone 416 in one or more patterns. In example aspects, the TPU material 610 may be deposited using a printing process where a liquid or semi-liquid TPU material is extruded from a printer head directly on to the reinforcement zone 416 in a pre-selected pattern. In example aspects, the TPU material 610 may include a recycled material that is in pellet form when introduced into the printer head. The composition of the recycled material and, by extension, the composition of the TPU material 610 may be adjusted or selected to produce a desired Shore A hardness. In example aspects, the Shore A hardness may be from about 40 A to about 80 A, from about 50 A to about 75 A, or from about 65 A to about 70 A. Selecting a Shore A hardness in this range provides a somewhat soft material that can better grip a ground surface. A Shore A hardness below, for example, 40 Shore A would generally not allow good adhesion to the surface of the reinforcement zone 416 (e.g., the TPU material is too soft), and having a Shore A hardness above, for example, 80 Shore A would generally be too hard which may be uncomfortable to the wearer and prevent the TPU material 610 from "gripping" a ground surface. In example aspects, the printer head may be heated to approximately 190 degrees Celsius to about 220 degrees Celsius, which melts the TPU pellets and enables the TPU material to be extruded.

When printing the TPU material 610 on to the reinforcement zone 416, the knit sleeve 100 may be stretched over a board to ensure an even application of the TPU material. In example aspects, two or more layers of the TPU material 610 may be deposited on the reinforcement zone 416. When depositing the initial layer of the TPU material 610, the printer head may be positioned closer to the surface of the reinforcement zone 416 as compared to when printing the subsequent layers. By positioning the printer head closer on the initial pass, the TPU material 610 may be at a hotter temperature as compared to when the printer head is located further away from the surface of the reinforcement zone 416. The hotter temperature of the TPU material 610 may act to partially melt or melt the TPU yarns that form the outer-facing surface 410 of the reinforcement zone 416. Because the TPU yarns and the TPU material 610 have the same or similar composition, the melted TPU material 610 and the partially melted TPU yarns may chemically bond together to help adhere the TPU material 610 to the reinforcement zone 416. In addition, positioning the printer head closer to the surface of the reinforcement zone 416 on the initial pass helps to force the liquid TPU material 610 into the actual knit structure of the reinforcement zone 416 creating a mechanical bond between the TPU material 610 and the yarns that form the reinforcement zone 416 as the TPU material 610 solidifies. This mechanical bond further helps to adhere the TPU material 610 to the reinforcement zone 416 and reduces the possibility of delamination during use. In example aspects, an additional two or more layers may be printed on top of the initial layer of the TPU material 610 to build up a thickness of from about 1 mm to about 5 mm. It is contemplated herein that the thickness of the TPU material 610 in different areas of the reinforcement zone 416 may be varied to achieve desired end properties as further described below.

As mentioned, the TPU material 610 is applied in a pattern such as the pattern generally indicated by reference numeral 611, the pattern indicated by reference numeral 612, and the pattern indicated by reference numeral 614. With respect to the pattern 611, the pattern 611 may extend to substantially cover the reinforcement zone 416 from a first side to a second side of the knit sleeve 100. Lateral edges 609 of the pattern 611 may be scalloped or notched in example aspects. The lateral edges 609 may be configured to wrap around the medial and lateral sides of a wearer's residual limb when the knit sleeve 100 is worn to provide an additional traction surface to these areas. This may be useful when the wearer is moving or rotating his residual limb such that the lateral and medial sides of the limb come into contact with a ground surface. Scalloping or notching the lateral edges 609, as opposed to having linear edges, exposes the reinforcement zone 416 at spaced-apart locations along the lateral edges 609. Because the knit sleeve 100 is flexible or pliable due to its knit structure and/or its yarn selection, this may provide for better articulation of the knit sleeve 100 as it wraps around the medial and lateral sides of the wearer's residual limb. The pattern 611 may further includes exposed areas 613 where the TPU material 610 is not applied to the underlying reinforcement zone 416. Again, better articulation of the knit sleeve 100 may be achieved by having the exposed areas 613 instead of a continuous coating of the TPU material 610.

The pattern 612, which may be optional, is positioned on the knit sleeve 100 such that it overlies the knee area of the wearer when the knit sleeve 100 is worn. Because the knee area is in contact with a ground surface and is a primary weight bearing location in certain wrestling stances, additional cushioning and/or grip may be desired in this area. As such, the pattern 612 may comprise multiple layers of the TPU material 610 to achieve a desired thickness that is greater than, for instance, the thickness of the TPU material 610 in the pattern 611. In addition, the TPU material 610 may be continuously applied (applied without gaps or openings) in the pattern 612 to provide enhanced cushioning and/or grip. Although the pattern 612 is shown as having a generally pentagon-type shape, it is contemplated herein that the pattern 612 may include other forms including logos and other types of branding.

The pattern 614 is, in example aspects, applied to the second end 112 of the knit sleeve 100. Although shown on the front aspect of the knit sleeve 100, it is contemplated herein that the pattern 614 may also extend on to the back aspect of the second end 112 of the knit sleeve 100. In example aspects, the pattern 614 is configured to cover or substantially cover (e.g., 90% or greater coverage) the knit structure 122. Similar to the pattern 612, the pattern 614 may comprise multiple layers of the TPU material 610 to achieve a desired thickness that is greater than, for example, the thickness of the TPU material 610 in the pattern 611. This reflects that the end of the residual limb of the wearer may sometimes act as the primary contact point with a ground surface during certain wrestling stances. As such, enhanced cushioning and grip may be desired in this area. Optionally, the TPU material 610 may be continuously applied (applied without gaps or openings) to provide enhanced cushioning and/or grip at the second end 112.

Figure 7A:
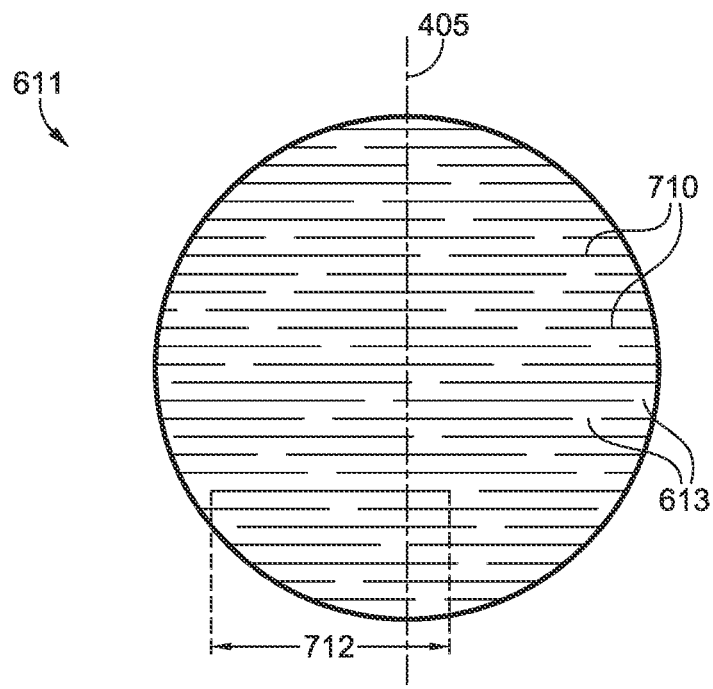
FIG. 7A illustrates a magnified view of a portion of the reinforcement zone of FIG. 6 in accordance with aspects herein.

FIG. 7A depicts a magnified view of the pattern 611. As shown, the TPU material 610 is deposited in a plurality of linear segments such as linear segments 710. The width of the linear segments 710 is illustrative, and it is contemplated herein that the linear segments 710 may comprise a greater width or a smaller width. A long axis of the linear segments 710, such as long axis 712 is oriented perpendicular to the axis 405 that extends from the first end 110 to the second end 112 of the knit sleeve 100 (shown in FIG. 7A). Orienting the long axes 712 of the linear segments 710 perpendicular or orthogonal to the axis 405 reflects that most of the forces that act on the reinforcement zone 416, and the linear segments 710 are due to forward and backward motions that are parallel to the axis 405 (i.e., the wearer shooting forward or being pushed back). For example, with respect to FIG. 3, the forces would generally correspond to the direction arrows 310 and 312. As such, orienting the linear segments 710 as described presents a large contact area to counteract the forward and backward forces and provide traction in the reinforcement zone 416.

The linear segments 710 are discontinuously applied such that the exposed areas 613 are formed between segments 710 located along the same line. In other words, the exposed areas 613 represents areas where the TPU material 610 is not applied to the reinforcement zone 416 thus exposing the underlying reinforcement zone 416. The exposed areas 613 in the pattern 611 may be random or they may form a pattern within the pattern 611 (e.g., the exposed areas 613 may form columns).

Figure 7B:
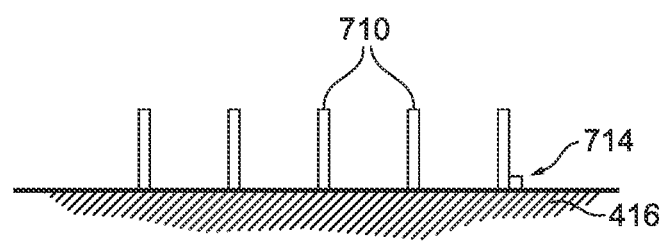
FIGS. 7B-7C illustrate example cross-sections of the thermoplastic polyurethane material as deposited on the reinforcement zone in accordance with aspects herein.
Figure 7C:
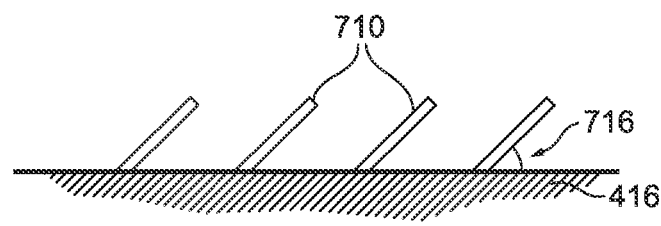

FIGS. 7B and 7C are example side views of the linear segments 710. In FIG. 7B, the linear segments 710 are shown extending perpendicularly away from the surface of the reinforcement zone 416. In other words, an angle, such as angle 714 between the base of the linear segment 710 and the reinforcement zone 416 is generally around 90 degrees. Orienting the linear segments 710 such that they are perpendicular to the surface of the reinforcement zone 416 generally provides equal traction when forces are applied to the knit sleeve 100 in a first direction and a second opposite direction parallel to the axis 405. In FIG. 7C, the linear segments 710 are oriented at an angle 716 less than 90 degrees. Orienting the linear segments 710 at an angle less than 90 degrees may provide unequal traction when forces are applied to the knit sleeve 100 in the first direction and the second opposite direction. Thus, the linear segments 710 may be oriented with respect to the surface of the reinforcement zone 416 such that they provide greater traction when the wearer shoots forward than when the wearer is being pushed backwards or vice versa.

Figure 8:
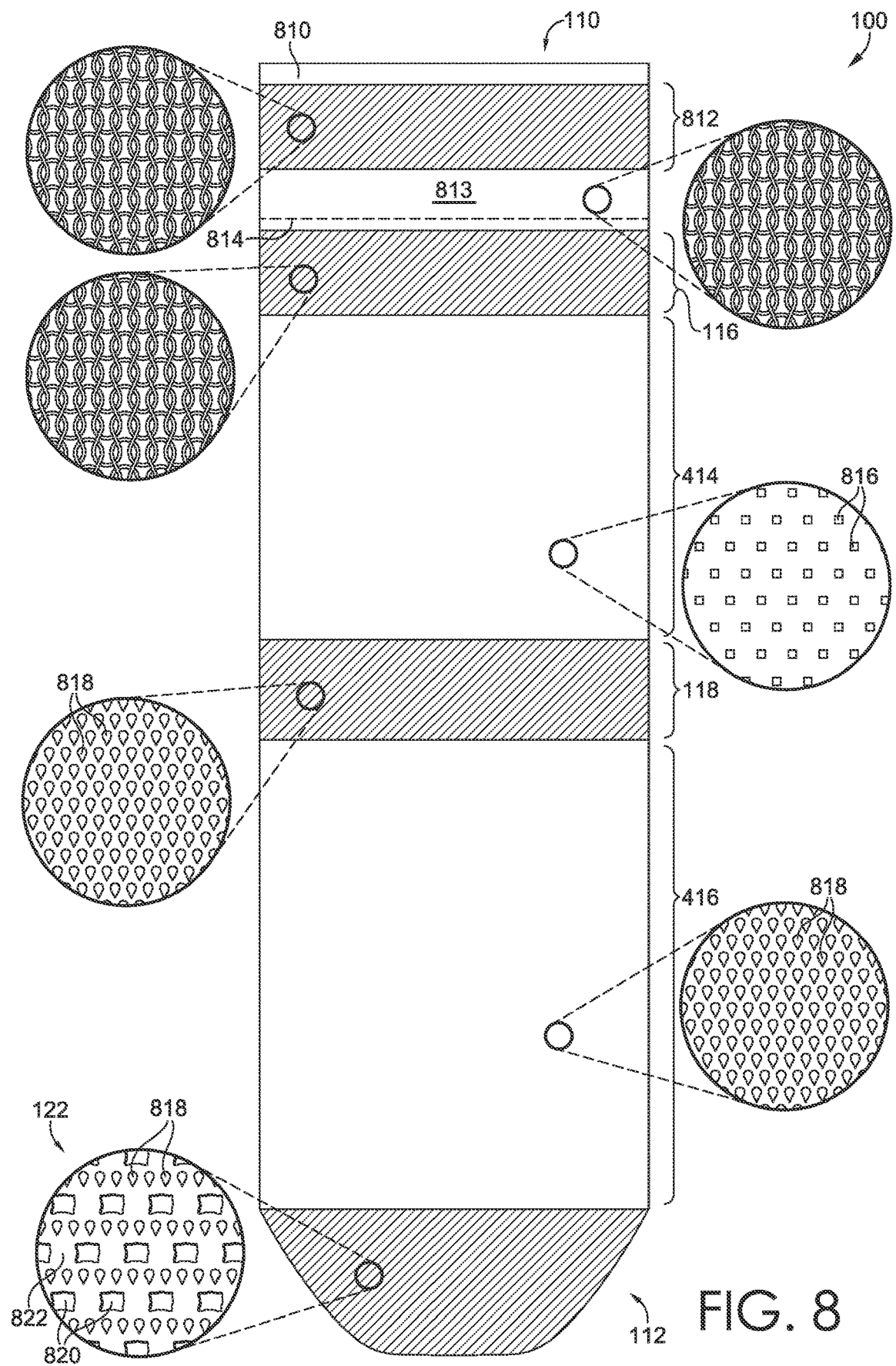
FIG. 8 illustrates a front view of the example tubular knit sleeve and depicts an inner-facing surface of the tubular knit sleeve in accordance with aspects herein.

FIG. 8 depicts a front aspect of an inner-facing surface 810 of the knit sleeve 100. FIG. 8 is provided to illustrate some of the surface details associated with the different zones and grip bands as well as to illustrate a welt grip band 812. As previously described, the welt zone 412 includes a two-layered construction with the exterior welt layer 413 and an interior welt layer 813 shown in FIG. 8. The welt zone 412 is formed by folding the interior welt layer 813 inwardly and securing it to the exterior welt layer 413 using, for example, stitching or linking knit stitches as indicated at reference numeral 814. In example aspects, the interior welt layer 813 includes the welt grip band 812. In example aspects, the welt grip band 812 may be knit using a welt set of grip yarns and a plating yarn. In example aspects, the plating yarn may comprise an elastic yarn covered with nylon. For example, the plating yarn may comprise a 78 decitex spandex yarn single covered with two strands of 78 decitex nylon. The welt grip band 812 may also include additional body yarns and/or plating yarns. In one example aspect, the additional yarn may comprise a polyester yarn such as four strands of 167 decitex polyester. Unlike the upper grip band 116, the middle grip band 118, and the lower grip band 210 which form a portion of both the outer-facing surface 410 and the inner-facing surface 810 of the knit sleeve 100, the welt grip band 812 forms a portion of just the inner-facing surface 810 and is absent from the outer-facing surface 410 due to the welt grip band 812 being knitted into the interior welt layer 813 of the welt zone 412. The welt grip band 812 may have a similar width as one or more of the upper grip band 116, the middle grip band 118, or the lower grip band 210. In example aspects, and as shown in the magnified view, the welt grip band 812 may be knit with a basic knit stitch without terry loops although other knit stitches are contemplated herein.

The upper grip band 116 is shown forming a portion of the inner-facing surface 810 of the knit sleeve 100. As shown in the magnified view, the upper grip band 116 may be knit with a basic knit stitch without terry loops in example aspects. As shown in the corresponding magnified view, the upper thigh zone 414 may be knit with a mesh knit structure having knit-in holes 816 to provide breathability and permeability.

The middle grip band 118 is shown forming a portion of the inner-facing surface 810 of the knit sleeve 100. In example aspects, and as shown in the magnified view, the middle grip band 118 is knit with terry loops, such as terry loops 818 that extend away from the inner-facing surface 810 to provide cushioning. In example aspects, the grip yarn may be used to form the terry loops 818. This increases the amount of exposed surface area of the grip yarn, which further facilitates the grip yarn's gripping function.

The reinforcement zone 416 is knit with terry loops as shown in the magnified view where the terry loops extend away from the inner-facing surface 810 to provide cushioning to this high contact area. The magnified view of the second end 112 macroscopically depicts what the knit structure 122 looks like. As explained further below, the offset areas 820 represent the areas where the body yarn is floated. The non-offset areas 822 include terry loops 818 that extend away from the inner-facing surface 810 for cushioning in this area. It is contemplated herein that the terry loops 818 may be formed in whole or in part from the grip yarns used in the knit structure 122 to further increase the gripping function of the second end 112 of the knit sleeve 100.

Figure 9:
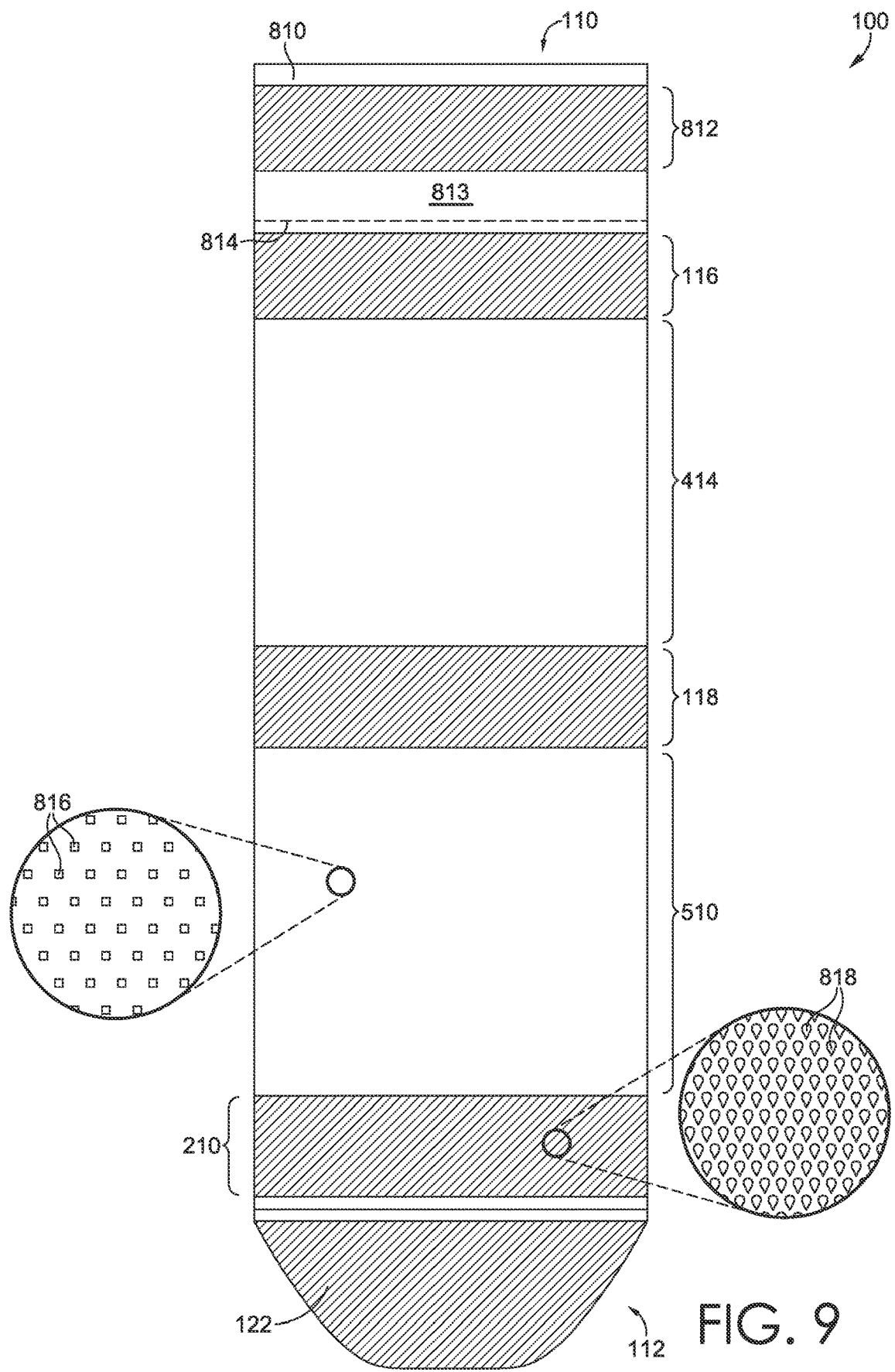
FIG. 9 illustrates a back view of the example tubular knit sleeve of FIG. 8 in accordance with aspects herein.

FIG. 9 depicts the inner-facing surface 810 of the back aspect of the knit sleeve 100. The welt grip band 812 is shown extending around a circumference of the knit sleeve 100. Features associated with the inner-facing surface 810 of the upper grip band 116, the upper thigh zone 414, and the middle grip band 118 are the same as that described with respect to FIG. 8 and will not be repeated here. The calf zone 510 may include a mesh knit structure as shown in the magnified view where the knit-in holes 816 provide permeability and breathability. The lower grip band 210 includes the terry loops 818 that extend from the inner-facing surface 810 to provide cushioning. It is contemplated herein that the terry loops 818 may be formed in whole or in part from the grip yarns further increasing the gripping function in this area. The description of the knit structure 122 at the second end 112 is the same as that described with respect to FIG. 8 and will not be repeated here.

Figure 10:
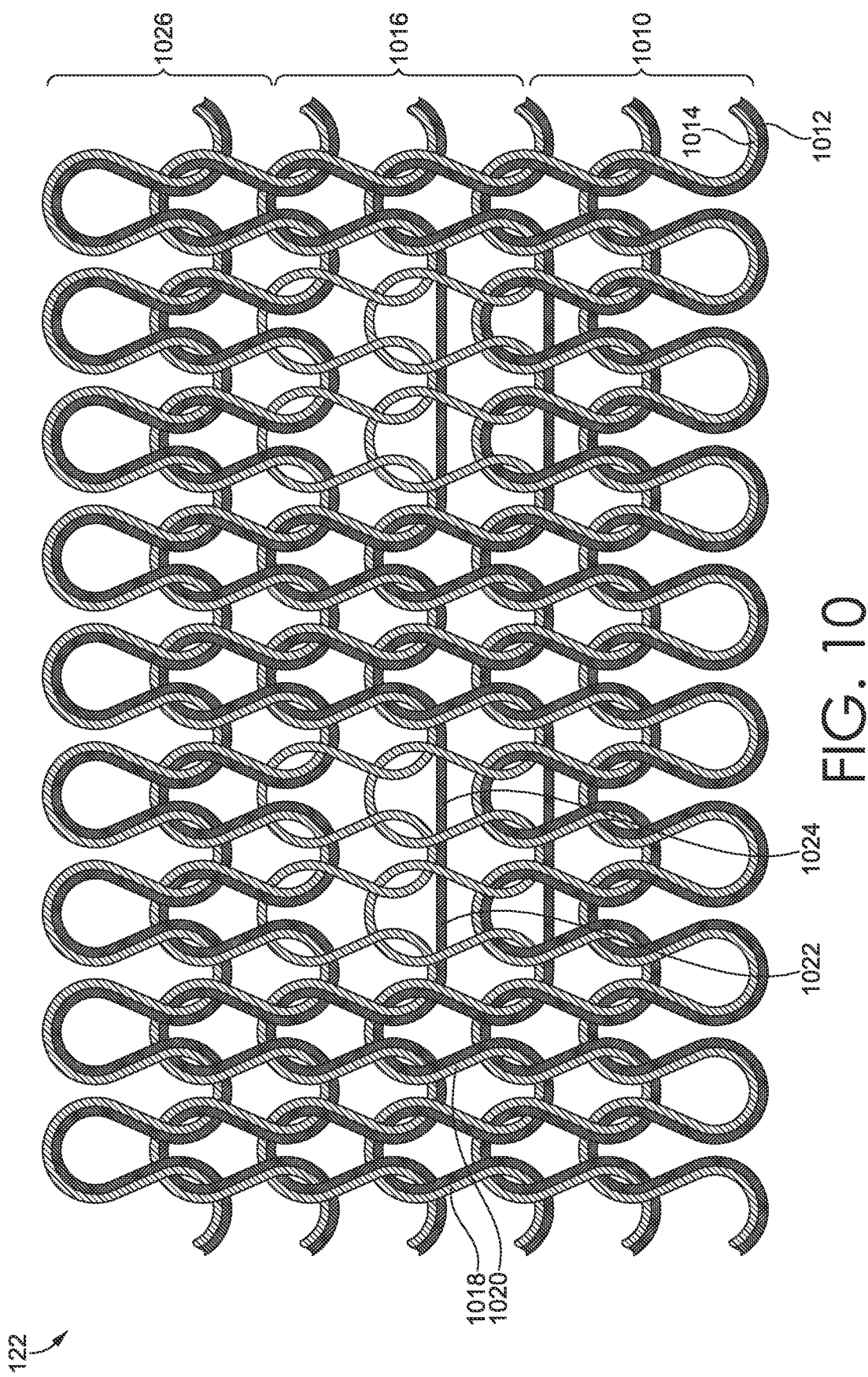
FIG. 10 illustrates a knit schematic of an example knit structure used to form a portion of the example tubular knit sleeve in accordance with aspects herein.

FIG. 10 depicts a knit schematic of the knit structure 122. Although the knit structure 122 is shown as being used to form the second end 112 of the knit sleeve 100, it is contemplated herein that the knit structure 122 may be used in other locations on the knit sleeve 100 or on others articles of apparel such as, for example, socks or sleeves for extremities. With respect to socks, the knit structure 122 may be used wherever additional compression is desired. Example locations include the toe end of the sock, a leg portion of the sock, and the like.

The knit structure 122 includes a first number of knit courses 1010 knit with a basic knit stitch using at least a body yarn 1012 (shown with cross-hatching) and a plating yarn 1014 (shown with hatching). In example aspects, the body yarn may comprise a grip yarn. Although not shown, it is contemplated herein that one or more of the body yarn 1012 and the plating yarn 1014 may be knit to form terry loops on the technical back of the knit structure 122 to provide cushioning as is known in the art of knitting. The first number of knit courses 1010 may comprise two courses as shown. In example aspects, the first number of knit courses 1010 may include more than two knit courses such as three knit courses, four knit courses, and the like. Or the first number of knit courses 1010 may include a fewer number of knit courses than shown, such as one knit course. The selection of the number of knit courses in the first number of knit courses 1010 may be based on desired end properties of the knit structure 122 such as, for example, increased or decreased cushioning.

Next, the knit structure 122 includes a second number of knit courses 1016 that have a repeating pattern of two basic knit stitches, such as knit stitches 1018 and 1020 knit with the body yarn 1012 and the plating yarn 1014, followed by two float stitches, such as float stitches 1022 and 1024 where the body yarn 1012 is floated across two wales while the plating yarn 1014 continues to be knit with a basic knit stitch, followed by two basic knit stitches knit with the body yarn 1012 and the plating yarn 1014, followed by two float stitches, and so on. Floating at least the body yarn 1012 increases the stretch resistance of the knit structure 122 (the knit structure 122 is more resistant to stretch) because there is less yarn available for stretching as compared to a knitted loop. This, in turn, increases the compression of the knit structure 122 which may be ideal for certain locations on the knit sleeve 100 (e.g., the second end 112 that encloses the end of the residual limb) or on a sock or on a sleeve for an extremity.

Although the second number of knit courses 1016 is shown comprising two knit courses, it is contemplated herein that the second number of knit courses 1016 may include additional knit courses such as three knit courses, four knit courses, and the like. It is further contemplated herein that the second number of knit courses 1016 may include the same number of knit courses as the first number of knit courses 1010 as shown in FIG. 10. It is also contemplated herein that the second number of knit courses 1016 may comprise a fewer number of knit courses than the first number of knit courses 1010 or a greater number of knit courses than the first number of knit courses 1010. The selection of the number of knit courses in the second number of knit courses 1016 may be based on desired end properties of the knit structure 122 such as, for example, increased or decreased resistance to stretch.

It is also contemplated herein that the body yarn 1012 may extend over a fewer number of wales or of a greater number of wales than that shown. By extending the body yarn 1012 over a fewer number of wales (e.g., one wale), the resistance to stretch may be decreased, and by extending the body yarn over a greater number of wales (e.g., greater than two wales), the resistance to stretch may be increased. It is additionally contemplated that the number of float stitches (two in this example) may differ from the number of basic knit stitches that immediately precede and/or follow the float stitches. Any and all aspects, and any variation thereof are contemplated as being within aspects herein.

The knit structure 122 next comprises a third number of knit courses 1026. The third number of knit courses 1026 may have the same features as the first number of knit courses 1010. The repeating pattern thus comprises a first number of knit courses having a basic knit stitch with terry loops, and a second number of knit courses where the body yarn is knit for a first number of stitches and then floated for a second number of stitches.

Figures 11, 12:
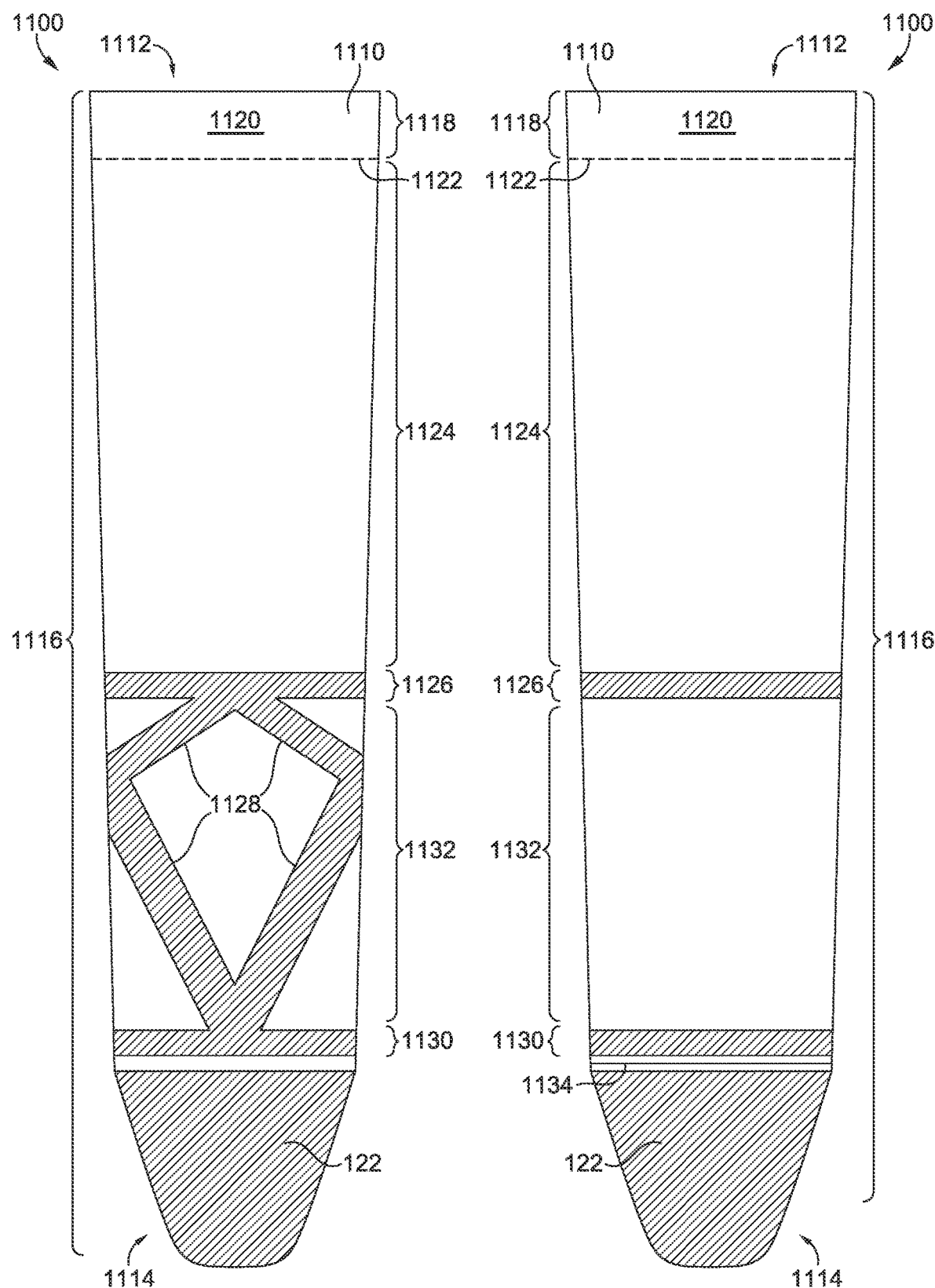
FIG. 11 illustrates a front view of an example tubular knit liner configured to be worn under the example tubular knit sleeve in accordance with aspects herein.
FIG. 12 illustrates a back view of the example tubular knit liner of FIG. 11 in accordance with aspect herein.

FIGS. 11 and 12 respectively depict views of a front aspect and a back aspect of a tubular knit liner 1100 that may optionally be worn under the knit sleeve 100 such that it is positioned between the knit sleeve 100 and the wearer's skin surface. In example aspects, the knit sleeve 100 and the knit liner 1100 may be sold together as part of a kit or system. The knit liner 1100 may be used to provide additional protection to the wearer's skin and/or to provide additional cushioning. In example aspects, the knit liner 1100 may have substantially the same length as the knit sleeve 100 such that the knit liner 1100 is fully covered or substantially covered by the knit sleeve 100.

FIG. 11 depicts a front aspect of an outer-facing surface 1110 of the tubular knit liner 1100 with the knit liner 1100 lying flat. The knit liner 1100 includes an open first end 1112, a closed second end 1114, and a tubular body 1116 extending between the first end 1112 and the second end 1114. The knit liner 1100 includes a welt zone 1118. Similar to the welt zone 412 of the knit sleeve 100, the welt zone 1118 includes an exterior welt layer 1120 and an interior welt layer (not shown) that is affixed to the exterior welt layer 1120 using, for example, stitching or linking stitches as indicated by reference numeral 1122. Further similar to the knit sleeve 100, the interior welt layer may include a welt grip band, such as the welt grip band 812 that is knit using a welt set of grip yarns. Because the welt grip band is knit into the interior welt layer, the welt grip band forms a portion of an inner-facing surface of the knit liner 1100 but does not form a portion of the outer-facing surface 1110 of the knit liner 1100. The welt grip band helps to secure the knit liner 1100 around an upper thigh area of a wearer such as the wearer 10.

The knit liner 1100 further includes an upper thigh zone 1124 that may be knit with a mesh knit structure having knit-in holes for permeability and breathability. In example aspects, the upper thigh zone 1124 may be knit with non-elastic yarns such as nylon yarns.

Below the upper thigh zone 1124, the knit liner 1100 includes a middle leg band 1126. In example aspects, instead of being knit with grip yarns, the middle leg band 1126 may be knit with elastic yarns for added compression in this area to prevent the knit liner 1100 from slipping or rotating. For example, the middle leg band 1126 may be knit with a 78 decitex spandex yarn single covered with two strands of 78 decitex nylon.

The front aspect of the knit liner 1100 may also optionally include a graphic image such as graphic image 1128 having a different color than remaining portions of the knit liner 1100. The graphic image 1128, in example aspects, may also be knit with an elastic yarn for added compression. In one example, the graphic image 1128 may be knit with a 78 decitex spandex yarn single covered with two strands of 78 decitex nylon. The knit liner 1100 further includes a lower leg band 1130 that may be knit with elastic yarns for added compression. In one example aspect, the lower leg band 1130 may be knit with a 78 decitex spandex yarn single covered with two strands of 78 decitex nylon. Using elastic yarns as opposed to grip yarns to form the middle leg band 1126, the graphic image 1128, and the lower leg band 1130 may allow for some freedom-of-movement between the knit sleeve 100 and the knit liner 1100 since the middle leg band 1126, the graphic image 1128, and the lower leg band 1130 are not "gripping" the knit sleeve 100. This, in turn, may improve wearer comfort.

The area of the knit liner 1100 located between the middle leg band 1126, the lower leg band 1130, and portions of the graphic image 1128 comprises a lower leg zone 1132 and may be knit with, for example, nylon yarns in a mesh knit structure for permeability and breathability. Similar to the knit sleeve 100, the second end 1114 of the knit liner 1100 includes the knit structure 122 and is tapered inwardly for added compression and a snug fit in this location.

The back aspect of the knit liner 1100 is shown in FIG. 12. The middle leg band 1126 is shown extending around a circumference of the tubular body 1116. The lower leg zone 1132, in example aspects, may not include a graphic image such as the graphic image 1128. The lower leg band 1130 is also shown extending around the circumference of the tubular body 1116. The knit structure 122 is shown extending on to the back aspect of the knit liner 1100. The knit liner 1100 also includes a seam 1134. Positioning the seam 1134 on the back aspect of the knit liner 1100 helps to prevent the seam 1134 from causing chaffing or coming into contact with a ground surface. Although not described, it is contemplated herein that the knit liner 1100 may be knit with additional yarns such as plating yarns and laid-in yarns for added structural stability and reinforcement.

Figure 13:
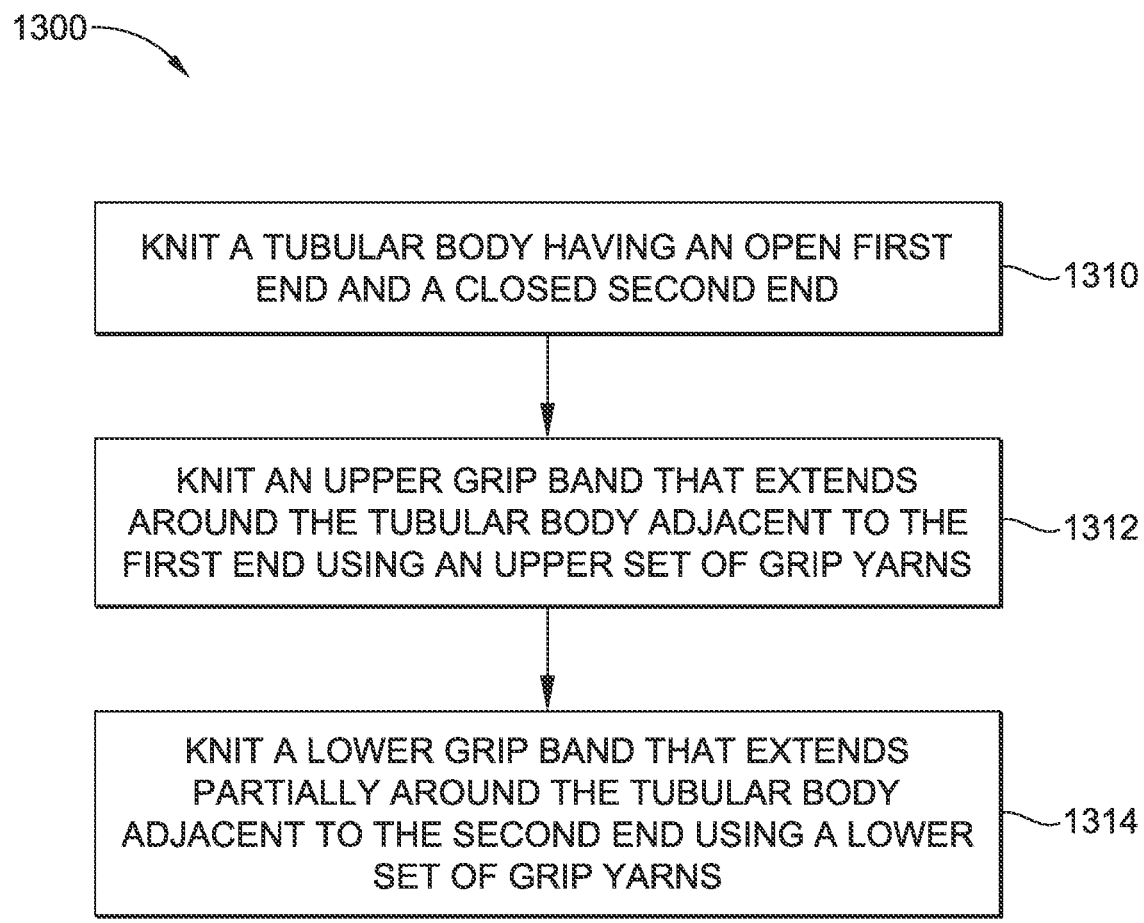
FIG. 13 illustrates a flow diagram of an example method of manufacturing the example tubular knit sleeve in accordance with aspects herein.

FIG. 13 depicts a flow diagram of an example method of manufacturing a knit sleeve for a below-the-knee amputee, such as the knit sleeve 100; the method of manufacturing is referenced generally by the numeral 1300. At a step 1310, a tubular body having an open first end and a closed second end, such as the tubular body 114 of the knit sleeve 100, is knit. In example aspects, the tubular body may be knit on a circular knitting machine such as a 120 needle, 5 inch, circular knitting machine. At a step 1312, an upper grip band, such as the upper grip band 116 is knit using an upper set of grip yarns. The upper grip band, in example aspects, may be located adjacent to the first end of the knit sleeve and may extend around a circumference of the tubular body. At a step 1314, a lower grip band, such as the lower grip band 210 is knit using a lower set of grip yarns. In example aspects, the lower grip band is located on a back aspect of the knit sleeve and extends only partially around the tubular body such that it is generally not located on the front aspect of the knit sleeve.

The method 1300 may include additional steps including knitting a middle grip band, such as the middle grip band 118 using a middle set of grip yarns. In example aspects, the middle grip band extends around the circumference of the tubular body. Additional steps may include knitting a reinforcement zone on the front aspect of the knit sleeve using TPU yarns. In example aspects, the reinforcement zone is located solely on the front aspect of the knit sleeve adjacent to the second end. An additional step may comprise depositing a TPU material, such as the TPU material 610, on to an outer-facing surface of the reinforcement zone to provide traction when the wearer shoots forward or is pushed back during wrestling maneuvers. The TPU material may be deposited using a printer head in example aspects.

The following clauses represent example aspects of concepts contemplated herein. Any one of the following clauses may be combined in a multiple dependent manner to depend from one or more other clauses. Further, any combination of dependent clauses (clauses that explicitly depend from a previous clause) may be combined while staying within the scope of aspects contemplated herein. The following clauses are illustrative in nature and are not limiting.

Clause 1. A tubular knit sleeve for a below-the-knee amputee, the tubular knit sleeve comprising: an open first end, a closed second end, and a tubular body extending between the first end and the second end; an upper grip band extending around a circumference of the tubular body adjacent to the first end, the upper grip band formed from an upper set of grip yarns; and a lower grip band extending partially around the circumference of the tubular body adjacent to the second end, the lower grip band located on a back aspect of the tubular knit sleeve, the lower grip band formed from a lower set of grip yarns.

Clause 2. The tubular knit sleeve according to clause 1, further comprising a middle grip band extending around the circumference of the tubular body and positioned between the upper grip band and the lower grip band, the middle grip band formed from a middle set of grip yarns.

Clause 3. The tubular knit sleeve according to any of clauses 1 through 2, wherein each of the upper set of grip yarns and the lower set of grip yarns comprises yarns having a denier per filament less than or equal to about 0.01.

Clause 4. The tubular knit sleeve according to any of clauses 1 through 3, wherein the upper grip band and the lower grip band each form a portion of an outer-facing surface of the tubular knit sleeve and a portion of an inner-facing surface of the tubular knit sleeve.

Clause 5. The tubular knit sleeve according to any of clauses 1 through 4, further comprising a welt grip band extending around the circumference of the tubular body and positioned between the upper grip band and the first end of the tubular knit sleeve, the welt grip band formed from a welt set of grip yarns.

Clause 6. The tubular knit sleeve according to clause 5, wherein the welt grip band forms a portion of an inner-facing surface of the tubular knit sleeve.

Clause 7. The tubular knit sleeve according to any of clauses 5 through 6, wherein the welt grip band does not form a portion of an outer-facing surface of the tubular knit sleeve.

Clause 8. The tubular knit sleeve according to any of clauses 1 through 7, wherein the lower grip band is absent from a front aspect of the tubular knit sleeve.

Clause 9. The tubular knit sleeve according to any of clauses 1 through 8, further comprising a reinforcement zone positioned on a front aspect of the tubular knit sleeve and located adjacent to the second end of the tubular knit sleeve, the reinforcement zone comprising thermoplastic polyurethane (TPU) yarns.

Clause 10. The tubular knit sleeve according to clause 9, further comprising a thermoplastic polyurethane (TPU) material deposited on an outer-facing surface of the reinforcement zone.

Clause 11. The tubular knit sleeve according to any of clauses 1 through 10, wherein the tubular body tapers from a first width to a second width less than the first width as the tubular body extends from the lower grip band to the second end.

Clause 12. A tubular knit sleeve for a below-the-knee amputee, the tubular knit sleeve comprising: an open first end, a closed second end, and a tubular body extending between the first end and the second end; a reinforcement zone positioned on a front aspect of the tubular knit sleeve adjacent to the second end of the tubular knit sleeve, the reinforcement zone comprising thermoplastic polyurethane (TPU) yarns; and a thermoplastic polyurethane (TPU) material deposited on an outer-facing surface of the reinforcement zone.

Clause 13. The tubular knit sleeve according to clause 12, wherein the TPU material is deposited in a pattern comprising a plurality of linear segments.

Clause 14. The tubular knit sleeve according to clause 13, wherein each linear segment of the plurality of linear segments has a long axis that is oriented perpendicular to an axis extending from the first end to the second end of the tubular knit sleeve.

Clause 15. The tubular knit sleeve according to any of clauses 12 through 14, wherein the TPU material is discontinuous such that there are a plurality of areas where the reinforcement zone is exposed.

Clause 16. The tubular knit sleeve according to any of clauses 12 through 15, further comprising at least one grip band extending around a circumference of the tubular body, the at least one grip band formed from a set of grip yarns.

Clause 17. A method of manufacturing a tubular knit sleeve for a below-the-knee amputee, the method comprising: knitting a tubular body having an open first end and a closed second end, wherein knitting the tubular body comprises: knitting an upper grip band that extends around a circumference of the tubular body adjacent to the first end, the upper grip band formed from an upper set of grip yarns; and knitting a lower grip band that extends partially around the circumference of the tubular body adjacent to the second end, the lower grip band located on a back aspect of the tubular knit sleeve, the lower grip band formed from a lower set of grip yarns.

Clause 18. The method of manufacturing the tubular knit sleeve according to clause 17, wherein knitting the tubular body further comprises knitting a reinforcement zone using thermoplastic polyurethane (TPU) yarns, the reinforcement zone located on a front aspect of the tubular knit sleeve and positioned adjacent to the second end.

Clause 19. The method of manufacturing the tubular knit sleeve according to clause 18, further comprising depositing a thermoplastic polyurethane (TPU) material on to an outer-facing surface of the reinforcement zone.

Clause 20. The method of manufacturing the tubular knit sleeve according to clause 19, wherein the TPU material is deposited by way of a printer head.

Clause 21. A sleeve system for a below-the-knee amputee, the sleeve system comprising: a tubular knit sleeve having an open first end, a closed second end, and a tubular body extending between the first end and the second end; an upper grip band extending around a circumference of the tubular body adjacent to the first end, the upper grip band formed from an upper set of grip yarns; and a lower grip band extending partially around the circumference of the tubular body adjacent to the second end, the lower grip band located on a back aspect of the tubular knit sleeve; and a tubular knit liner adapted to be worn under the tubular knit sleeve, the tubular knit liner having an open first end, a closed second end, and a tubular body extending between the first end and the second end; and a welt grip band extending around a circumference of the tubular body adjacent to the first end of the tubular knit liner, the welt grip band knit using a welt set of grip yarns.

Clause 22. The sleeve system according to clause 21, wherein the tubular knit sleeve further comprises a middle grip band extending around the circumference of the tubular body and positioned between the upper grip band and the lower grip band, the middle grip band formed from a middle set of grip yarns.

Clause 23. The sleeve system according to any of clauses 21 through 22, the tubular knit sleeve further comprising a welt grip band extending around the circumference of the tubular body and positioned between the upper grip band and the first end of the tubular knit sleeve, the welt grip band formed from a welt set of grip yarns.

Clause 24. The sleeve system according to clause 23, wherein each of the welt grip band of the tubular knit sleeve and the welt grip band of the tubular knit liner forms a portion of an inner-facing surface of the respective tubular knit sleeve and the tubular knit liner, and wherein each of the welt grip band of the tubular knit sleeve and the welt grip band of the tubular knit liner does not form a portion of an outer-facing surface of the respective tubular knit sleeve and the tubular knit liner.

Clause 25. The sleeve system according to any of clauses 21 through 24, wherein the tubular knit sleeve comprises a reinforcement zone positioned on a front aspect of the tubular knit sleeve and located adjacent to the second end of the tubular knit sleeve, the reinforcement zone comprising thermoplastic polyurethane (TPU) yarns.

Clause 26. The sleeve system according to clause 25, further comprising a TPU material deposited on an outer-facing surface of the reinforcement zone.

Clause 27. The sleeve system according to any of clauses 21 through 26, wherein the tubular body of each of the tubular knit sleeve and the tubular knit liner tapers inwardly at the respective second ends of the tubular knit sleeve and the tubular knit liner.

Clause 28. The sleeve system according to any of clauses 21 through 27, wherein the tubular knit liner includes a middle leg band that extends around a circumference of the tubular body and is located approximately midway between the first end and the second end, the middle leg band knit using elastic yarns.

Clause 29. The sleeve system according to any of clauses 21 through 28, wherein the tubular knit liner includes a lower leg band that extends around a circumference of the tubular body and is located adjacent to the second end, the lower leg band knit using elastic yarns.

Clause 30. The sleeve system according to any of clauses 21 through 29, wherein a length of the tubular knit sleeve is approximately the same as a length of the tubular knit liner.

Clause 31. A knit structure for an article of apparel, the knit structure comprising: a repeating pattern of a first number of knit courses having a body yarn and a plating yarn, the body yarn and the plating yarn knit in a basic knit stitch; and a second number of knit courses integrally knit with the first number of knit courses, the second number of knit courses having the body yarn and the plating yarn, wherein within each knit course of the second number of knit courses the body yarn is knit in a repeating pattern comprising a first number of knit stitches knit with a basic knit stitch and a second number of knit stitches knit with a float stitch.

Clause 32. The knit structure according to clause 31, wherein the plating yarn is continuously knitted in a basic knit stitch in the second number of knit courses, and wherein the body yarn forms the float stitch in the second number of knit courses.

Clause 33. The knit structure according to any of clauses 31 through 32, wherein one or more of the body yarn and the plating yarn form terry loops in the first number of knit courses.

Clause 34. The knit structure according to any of clauses 31 through 33, wherein the first number of knit stitches is a same number of knit stitches as the second number of knit stitches.

Clause 35. The knit structure according to any of clauses 31 through 33, wherein the first number of knit stitches is a different number of knit stitches than the second number of knit stitches.

Clause 36. The knit structure according to any of clauses 31 through 35, wherein the first number of knit courses is a same number of knit courses as the second number of knit courses.

Clause 37. The knit structure according to any of clauses 31 through 35, wherein the first number of knit courses is a different number of knit courses than the second number of knit courses.

Clause 38. The knit structure according to any of clauses 31 through 37, wherein the article of apparel is a tubular knit sleeve or a tubular knit liner for a below-the-knee amputee.

Clause 39. The knit structure according to clause 38, wherein the knit structure is located at a closed second end of the tubular knit sleeve or the tubular knit liner.

Clause 40. The knit structure according to any of clauses 31 through 37, wherein the article of apparel is a sock.

Clause 41. The knit structure according to clause 40, wherein the knit structure is located at a toe end of the sock.

Clause 42. The knit structure according any of clauses 40 through 41, wherein the knit structure is located at a leg portion of the sock.

Clause 43. An article of apparel having the knit structure of clause 31, wherein the article of apparel comprises one of a tubular knit sleeve for a below-the-knee amputee, a tubular knit liner for a below-the-knee amputee, a sock, or a sleeve for an extremity.

Aspects of the present disclosure have been described with the intent to be illustrative rather than restrictive. Alternative aspects will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described.

What is claimed is:

1. A tubular knit sleeve for a below-the-knee amputee, the tubular knit sleeve comprising:
   an open first end, a closed second end, and a tubular body extending between the first end and the second end;
   an upper grip band extending around a circumference of the tubular body adjacent to the first end, the upper grip band formed from an upper set of grip yarns having a denier per filament less than or equal to about 0.01; and
   a lower grip band extending partially around the circumference of the tubular body adjacent to the second end, the lower grip band located on a back aspect of the tubular knit sleeve, the lower grip band formed from a lower set of grip yarns having a denier per filament less than or equal to about 0.01;
   wherein the lower grip band comprises a single jersey knit structure with terry loops; and
   wherein the lower grip band further comprises a plating yarn comprising a 156 decitex spandex yarn covered with two strands of 78 decitex nylon.

2. The tubular knit sleeve of claim 1, further comprising a middle grip band extending around the circumference of the tubular body and positioned between the upper grip band and the lower grip band, the middle grip band formed from a middle set of grip yarns.

3. The tubular knit sleeve of claim 1, wherein the upper grip band and the lower grip band each form a portion of an outer-facing surface of the tubular knit sleeve and a portion of an inner-facing surface of the tubular knit sleeve.

4. The tubular knit sleeve of claim 1, further comprising a welt grip band extending around the circumference of the tubular body and positioned between the upper grip band and the first end of the tubular knit sleeve, the welt grip band formed from a welt set of grip yarns.

5. The tubular knit sleeve of claim 4, wherein the welt grip band forms a portion of an inner-facing surface of the tubular knit sleeve.

6. The tubular knit sleeve of claim 5, wherein the welt grip band does not form a portion of an outer-facing surface of the tubular knit sleeve.

7. The tubular knit sleeve of claim 1, wherein the lower grip band is absent from a front aspect of the tubular knit sleeve.

8. The tubular knit sleeve of claim 1, further comprising a reinforcement zone positioned on a front aspect of the tubular knit sleeve and located adjacent to the second end of the tubular knit sleeve, the reinforcement zone comprising thermoplastic polyurethane (TPU) yarns.

9. The tubular knit sleeve of claim 8, further comprising a thermoplastic polyurethane (TPU) material deposited on an outer-facing surface of the reinforcement zone.

10. The tubular knit sleeve of claim 1, wherein the tubular body tapers from a first width to a second width less than the first width as the tubular body extends from the lower grip band to the second end.

11. A tubular knit sleeve for a below-the-knee amputee, the tubular knit sleeve comprising:
- an open first end, a closed second end, and a tubular body extending between the first end and the second end;
- a reinforcement zone positioned on a front aspect of the tubular knit sleeve adjacent to the second end of the tubular knit sleeve, the reinforcement zone comprising thermoplastic polyurethane (TPU) yarns; and
- a thermoplastic polyurethane (TPU) material deposited on an outer-facing surface of the reinforcement zone;
- wherein the reinforcement zone comprises a single jersey knit structure with terry loops using one strand of a 100 decitex TPU yarn in combination with a polyester body yarn comprising four strands of 167 decitex polyester.

12. The tubular knit sleeve of claim 11, wherein the TPU material is deposited in a pattern comprising a plurality of linear segments.

13. The tubular knit sleeve of claim 12, wherein each linear segment of the plurality of linear segments has a long axis that is oriented perpendicular to an axis extending from the first end to the second end of the tubular knit sleeve.

14. The tubular knit sleeve of claim 11, wherein the TPU material is discontinuous such that there are a plurality of areas where the reinforcement zone is exposed.

15. The tubular knit sleeve of claim 11, further comprising at least one grip band extending around a circumference of the tubular body, the at least one grip band formed from a set of grip yarns.

16. A method of manufacturing a tubular knit sleeve for a below-the-knee amputee, the method comprising:
knitting a tubular body having an open first end and a closed second end, wherein knitting the tubular body comprises:
- knitting an upper grip band that extends around a circumference of the tubular body adjacent to the first end, the upper grip band formed from an upper set of grip yarns having a denier per filament less than or equal to about 0.01; and
- knitting a lower grip band that extends partially around the circumference of the tubular body adjacent to the second end, the lower grip band located on a back aspect of the tubular knit sleeve, the lower grip band formed from a lower set of grip yarns having a denier per filament less than or equal to about 0.01; and
- wherein the lower grip band comprises a single jersey knit structure with terry loops; and
- wherein the lower grip band further comprises a plating yarn comprising a 156 decitex spandex yarn covered with two strands of 78 decitex nylon.

17. The method of manufacturing the tubular knit sleeve of claim 16, wherein knitting the tubular body further comprises knitting a reinforcement zone using thermoplastic polyurethane (TPU) yarns, the reinforcement zone located on a front aspect of the tubular knit sleeve and positioned adjacent to the second end.

18. The method of manufacturing the tubular knit sleeve of claim 17, further comprising depositing a thermoplastic polyurethane (TPU) material on to an outer-facing surface of the reinforcement zone.

19. The method of manufacturing the tubular knit sleeve of claim 18, wherein the TPU material is deposited by way of a printer head.

* * * * *